(12) United States Patent
Abel

(10) Patent No.: US 7,909,763 B2
(45) Date of Patent: Mar. 22, 2011

(54) NEONATAL NUTRITION ASSESSMENT SYSTEM

(75) Inventor: Deborah M. Abel, Franklin, IN (US)

(73) Assignee: Deborah M. Abel, Franklin, IN (US)

( * ) Notice: Subject to any disclaimer, the term of this patent is extended or adjusted under 35 U.S.C. 154(b) by 1438 days.

(21) Appl. No.: 11/330,668

(22) Filed: Jan. 12, 2006

(65) Prior Publication Data

US 2007/0161870 A1 Jul. 12, 2007

(51) Int. Cl.
*A61B 5/00* (2006.01)
(52) U.S. Cl. ............................. 600/300; 705/3; 128/921
(58) Field of Classification Search .................... None
See application file for complete search history.

(56) References Cited

U.S. PATENT DOCUMENTS

| 5,954,640 A * | 9/1999 | Szabo ........................... 600/300 |
| 2004/0176667 A1 * | 9/2004 | Mihai et al. .................... 600/300 |
| 2005/0171503 A1 * | 8/2005 | Van Den Berghe et al. .. 604/504 |

* cited by examiner

*Primary Examiner* — Eric F Winakur
*Assistant Examiner* — Bobby Soriano
(74) *Attorney, Agent, or Firm* — Taft, Stettinius & Hollister, LLP; Keith J. Swedo

(57) ABSTRACT

A neonatal nutrition assessment system is disclosed that includes a remote terminal connected with a server as well as several software modules. A patient diagnosis module operable to allow a physician to record at least one diagnosis relating to a patient with the remote terminal. A parenteral nutrition software module operable to allow the physician to record a parenteral nutrition prescription for a predetermined time period including at least one parenteral nutrition solution to be given the patient. An enteral nutrition software module operable to allow the physician to record an enteral nutrition prescription for the predetermined time period including at least one enteral nutrition solution to be given the patient. An outputs software module operable to allow a user to record a plurality of bodily output values for the patient over the predetermined time period. A medication software module operable to allow the physician to record at least one medication prescription for the patient. A laboratory software module operable to record a plurality of lab results for the patient over the predetermined time period.

12 Claims, 21 Drawing Sheets

Neonatal Nutrition Assessment System

Daily Pediatric Parenteral Nutrition Order

| | January 10, 2005 | | January 11, 2005 | | January 12, 2005 | | January 13, 2005 | |
|---|---|---|---|---|---|---|---|---|
| 160 | Cen | ☐ | Cen | ☐ | Cen | ☐ | Cen | ☐ |
| 162 | Per | ☐ | Per | ☑ | Per | ☐ | Per | ☐ |
| 164 | Na | | Na | 4 | Na | | Na | |
| 166 | K | | K | 3.5 | K | | K | |
| 168 | Cl | ☐ | Cl | ☐ | Cl | ☐ | Cl | ☑ |
| 170 | P | 1.0 | P | 1.9 | P | | P | |
| 172 | Ca | | Ca | 2.2 | Ca | | Ca | 2.2 |
| 174 | Mg | | Mg | | Mg | | Mg | |
| 176 | MVI | ☐ | MVI | ☑ | MVI | ☐ | MVI | ☐ |
| 178 | TES | ☐ | TES | ☑ | TES | ☐ | TES | ☑ |
| 180 | Zn | ☐ | Zn | ☐ | Zn | ☐ | Zn | ☐ |
| 182 | Ranit | ☐ | Ranit | ☐ | Ranit | ☐ | Ranit | ☐ |
| 184 | Carn | ☐ | Carn | ☐ | Carn | ☐ | Carn | ☐ |
| 186 | Hep | ☐ | Hep | ☐ | Hep | ☑ | Hep | ☐ |
| 188 | Other | ☐ | Other | ☐ | Other | ☐ | Other | ☐ |

| | | | | | | |
|---|---|---|---|---|---|---|
| 192 PN Dosing Weight (kg) | 1.5 | | 1.5 | | 1.5 | | 1.5 |
| 194 Hours to be used in rate calculation | 24 | | 24 | | 24 | | 24 |
| 196 Order Infusion Rate (PN Script) mL/Hour | 6 | | 6 | | 6 | | 7 |
| 198 Physician Rx mL/Hour, % (Rx Script) | 4 | 67% | 6 | 100% | 6 | 100% | 7 | 100% |
| Volume mL/kg | 96 | | 96 | | 96 | | 96 |

127 — Save / Update    Main Menu — 55

Figure 8

Daily Pediatric Parenteral Nutrition Order

| | | | | | | |
|---|---|---|---|---|---|---|
| Total PN Volume (mL) | 160 | 308 | 242 | 197 |
| Total PN mL/kg (Actual Weight) | 48 | 91 | 70 | 59 |
| Total PN mL/kg (Dosing Weight) | 53 | 103 | 81 | 66 |
| Total PN kcal | 85 | 280 | 204 | 154 |
| Total PN kcal/kg (Actual Weight) | 26 | 82 | 59 | 46 |
| Total PN kcal/kg (Dosing Weight) | 28 | 93 | 68 | 51 |
| Total Projected PN Volume (mL/kg) | 0 | 100 | 100 | 100 |
| Total Projected PN Calories (kcal/kg) | 0 | 114 | 114 | 114 |

| | | | | | | |
|---|---|---|---|---|---|---|
| Total PN Protein (g/kg/day) (Dosing Weight) | 1.98 | 3.81 | 3.10 | 2.65 | 2.83 | 3.00 |
| Average PN Protein for past N days (g/kg) | N= | 3 | Start Date | 7/9/2004 | End Date | 7/12/2004 | Results | 3.49 g/kg/day |
| NPC:N ratio | 202 | 202 | 202 | 202 | 202 | 202 | 20233 |

Figure 10

Medications

Meds

| Name | Dosage | Date | Name | Date | Name | Dosage | Date | Name | Dosage |
|---|---|---|---|---|---|---|---|---|---|
| Ammonium Chloride | | | Calcium Bicarbonate | | | | | Calcium Gluconate | |
| Calcium Lactate | | | Carnitine | | | | | Ferinsol | |
| Potassium Chloride | | | Potassium Phosphate | | | | | Pediatric Multivitamin w/ | |
| Pediatric Multivitamin | | | Reglan | | | | | Sodium Chloride | |
| Sodium Phosphate | | | Other | | | | | Other | |

| Name | Date | Name | Date | Name | Dosage | Date | Name |
|---|---|---|---|---|---|---|---|
| Albuterol | | Ampicillin | | Ativan | | | Atrovent |
| Cafehut | | Dexamethasone | | Digoxin | | | Dopamine |
| Fentanyl | | Gentamycin | | Hydralazine | | | Hydrochlorothiazide |
| Indocin | 7/5/2004 | Lasix | 7/1/2004 | Morphine | | | Phenobarbital |
| OVAR | | Ranitidine | | Sodium Bicarbonate | | | Survanta |
| Versed | | Zantac | | Cefotaxime | | | Other |
| Dobutamine | | Vancomicin | | | | | |

Save / Update   Main Menu

Figure 15

NEONATAL NUTRITION ASSESSMENT SYSTEM

BACKGROUND OF THE INVENTION

1. Technical Field

The present invention relates generally to neonatal nutrition and more particularly, to a method and system that will record, calculate, and assist the clinician in problem solving giving a variety of clinical options to feed fragile infants in a Neonatal Intensive Care Unit ("NICU").

2. Related Art

Providing adequate and proper nutrition to infants is extremely important in the first few days, weeks and months of life. Of course, it is always important to provide adequate nutrition to infants, but in the case of babies born early and/or with medical complications, it is much more important. Typically, a baby that is born well in advance of his or her due date may be seriously underdeveloped and underweight. Gestation, associated with the time of birth, is often referred to as following into one of the following categories: Preterm (less than 37 weeks), Term (37-42 weeks), and Post-term (greater than 42 weeks). Physical size for gestational age is referred to as Small (weight less than 10th percentile), Appropriate (weight greater than 10th percentile and <90th percentile), and Large (weight greater than 90th % percentile. As it relates to low birth weight, babies traditionally fall into one category or population. These populations include Low Birth Weight ("LBW") (1500 g-2500 g), Very Low Birth Weight ("VLBW") (1000 g-1499 g), and Extremely Low Birth Weight ("ELBW") (<1000 g).

As set forth above, providing adequate nutrition to LBW, VLBW, and ELBW infants presents significant challenges because of the physiological immaturity and severe medical complications often encountered with these infants. These infants may range in weight from about 500-1,500 grams (1.1 lbs.-3.3 lbs.) and may range in gestational age from about 24 weeks to 38 weeks. Premature infants, by definition, have a gestational age less than thirty-eight weeks and usually weigh less than 2,500 grams.

As a result of the difficulty experienced in providing nutrition to this category of infants, nutrition care protocols and guidelines have been developed and continue to develop that are designed to address the nutritional needs of these special infants. The protocols are based on various factors including specific clinical parameters and laboratory values. For example, the amount and type of fluid provided to these infants may be predicated upon the gestational age, weight, urine output, urine specific gravity, and serum electrolyte values, as well as medical status (renal function, cardiovascular symptoms, and so forth).

Vast amounts of clinical and laboratory data are typically collected daily in association with each infant. The clinical and laboratory data are critical tools that are used by physicians to diagnose and treat each infant. The data may take the form of vital signs, neurological signs, intake and output, respiratory settings, hematological data, chemistry data, blood gases and so forth. The ability of the medical team to provide quality care for these infants depends, in large part, upon the easy accessibility of this data.

In current practice, paper forms are often used for recording clinical and laboratory data in neonatal intensive care units ("NICUs"). The nutrition assessment forms include information relating to dates, weight measurements, parental nutrition intakes, enteral nutrition intakes, outputs, lab values, medications, and so forth. Although these forms provide valuable data to physicians, they reduce the amount of time available for patient treatment and often result in numerous searches for relevant information by attending physicians, surgeons, dietitians, neonatal nurse practitioners, residents, nurses, respiratory therapists, and other health care team providers. In addition, because several sections of forms must be filled in by making calculations or looking up relevant data, often by different people, the forms are prone to erroneous entries.

The average length of hospitalization required by these VLBW special infants in a NICU is around 100 days with an average cost of $1 million. They are typically born with immature organs including the lungs and digestive systems and thus specialized critical care nutrition is essential for these babies to grow, fully develop organ systems, respond to medical treatment and survive.

As a result of the aforementioned problems, a need exists for a neonatal nutrition assessment system that is capable of easily and quickly providing critical care givers with real time access to the entire diagnosis and treatment parameters for each infant in a NICU.

SUMMARY OF THE INVENTION

The present invention discloses a neonatal nutrition assessment system that efficiently converts nutritional data into usable clinical information within a NICU. The average length of hospitalization of VLBW infants in a NICU is 100 days with an average cost of $1 million. They are born with immature organs including the lungs and digestive systems and thus specialized critical care nutrition is essential for these babies to grow, fully develop organ systems, respond to medical treatment and survive. The neonatal nutrition assessment system will record, calculate, and create a variety of solutions or options to feed these medically fragile babies. The neonatal nutrition assessment system is uniquely capable of tracking all of the essential nutrition/feeding/growth history and the baby's response to parenteral (nutrients given by vein) and enteral (nutrients given through gastrointestinal tract (GI) either through a tube or taken orally) nutrition. The present invention revolutionizes the ability of the physician and health care team to make informed decisions based on real time clinical data linked to the past medical/nutrition/feeding history of any given infant in the NICU as well as the ability to respond to the on-going clinical changes with the documentation of these changes and their outcomes in clinical management.

The present invention discloses a neonatal nutrition assessment system. The neonatal nutrition assessment system may include a remote terminal connected with a server. A diagnosis module may be included that is operable to allow a physician to record numerous diagnoses relating to a patient using the remote terminal. The data associated with the patient may be transmitted to and stored on the server as the remote terminals may comprise a wireless pocket PC or notepad PC. The neonatal nutrition assessment system may also include a parenteral nutrition software module that may be operable to allow the physician to record and/or prescribe a parenteral nutrition prescription for a predetermined time period including at least one parenteral nutrition solution to be given the patient. An enteral nutrition software module that may be operable to allow the physician to record and/or prescribe an enteral nutrition prescription for the predetermined time period including at least one enteral nutrition solution to be given the patient.

The neonatal nutrition assessment system may also include an outputs software module that may be operable to allow a user to record a plurality of bodily output values for the patient over the predetermined time period. In addition, a medication software module that may be included that is operable to allow the physician to record and/or prescribe at least one medication prescription for the patient. The neonatal nutrition assessment system may also include a laboratory software module that may be operable to record a plurality of lab results for the patient over the predetermined time period.

The present invention also discloses a nutrition assessment system that includes a remote terminal connected with a database server. A parenteral nutrition module is operable to automatically calculate a plurality of parenteral nutrient intake data values relative to weight and bodily functions of a patient. An enteral nutrition module is operable to automatically calculate a plurality of enteral nutrient intake data values relative to weight and bodily functions of the patient. A parenteral and enteral nutrition module is operable to integrate the plurality of parenteral and enteral nutrient intake data values. Another module is operable to integrate a plurality of demographic data values with the plurality of parenteral and enteral nutrient intake data values. A report module is operable to compare a plurality of data values associated with the patient with normative data values and guidelines. The nutrition assessment system allows caretakers to view the history of treatment as it relates to a patient so that proper care decisions and diagnosis may be made in relation to the patient.

Other systems, methods, features and advantages of the invention will be, or will become apparent to one with skill in the art upon examination of the following figures and detailed description. It is intended that all such additional systems, methods, features and advantages be included within this description, be within the scope of the invention, and be protected by the following claims.

BRIEF DESCRIPTION OF THE DRAWINGS

The components in the figures are not necessarily to scale, emphasis instead being placed upon illustrating the principles of the invention. Moreover, in the figures, like reference numerals designate corresponding parts throughout the different views.

FIG. 8 represents an illustrative parenteral nutrition order graphical user interface of the NNA software application.

FIG. 10 represents an illustrative total parenteral nutrition graphical user interface of the NNA software application.

FIG. 15 represents an illustrative medications graphical user interface of the NNA software application.

DETAILED DESCRIPTION OF THE PRESENTLY PREFERRED EMBODIMENTS

Figure 1:
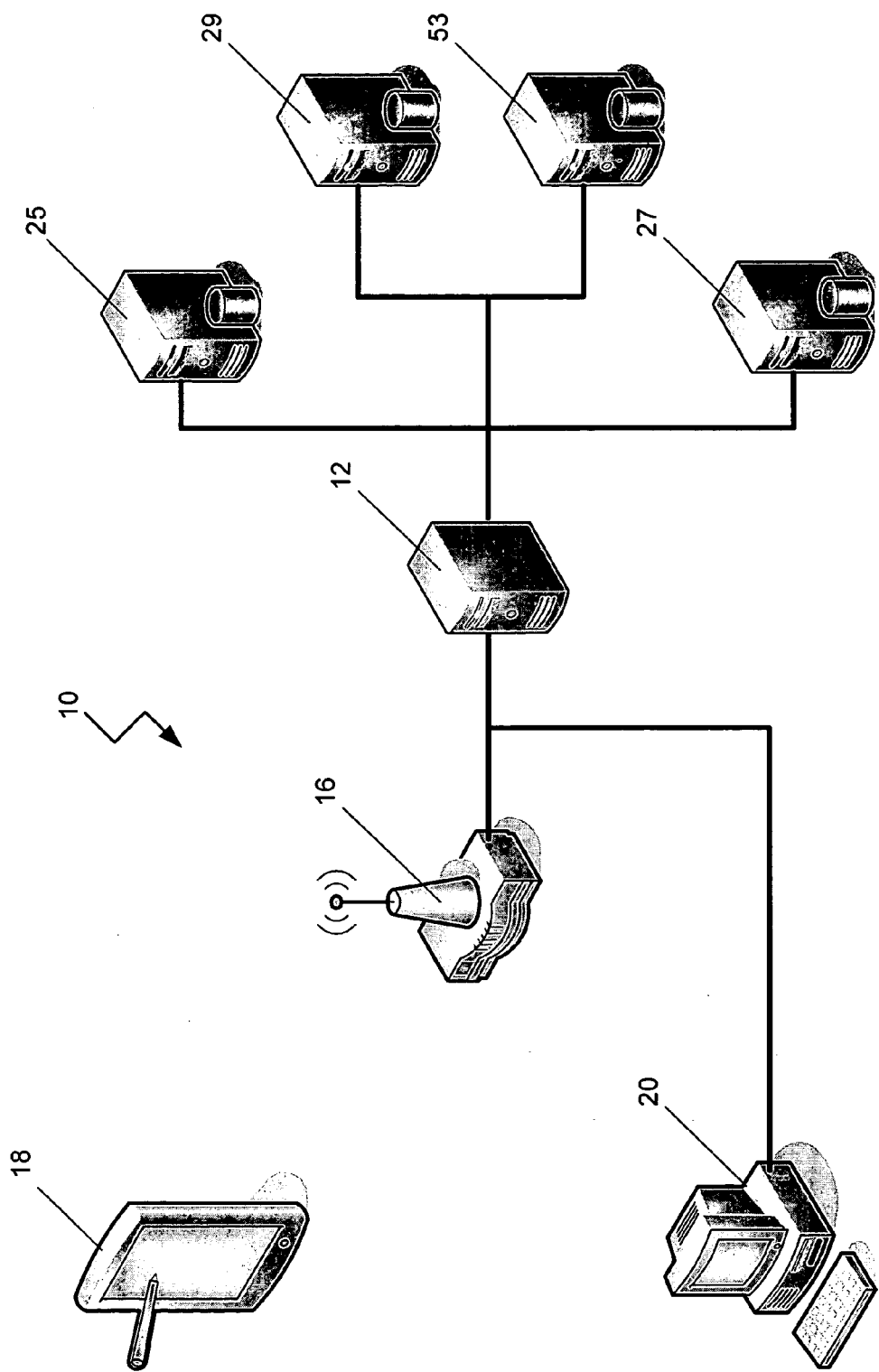
FIG. 1 illustrates a hardware view of an illustrative embodiment of the NNA system.

Referring to FIG. 1, an illustrative hardware configuration for a neonatal nutrition assessment ("NNA") system 10 that is capable of recording, calculating, charting, and assisting physicians create a variety of solutions or feeding options for medically fragile infants is illustrated. The NNA system 10 is operable to provide a history of what was fed to the infant and how many calories it took for the baby to grow parentally, enterally, or through a combination of both. The NNA system 10 assists physicians and care givers to make critical decisions and allows decisions to be based on accurate, efficient, consistent and easily accessible information. This results in healthier infants, shorter stays in the NICU, reduced costs, and historical tracking of results based on feeding decisions made for infants with particular diagnosis.

The NNA system 10 may include a NNA server 12 that has a NNA software application 14 (see FIG. 2) that is operable to perform a plurality of tasks, which are set forth in greater detail below. The NNA server 12 may be connected with a wireless router 16 that is operational to wirelessly transmit and receive data between the NNA server 12 and a variety of different devices, such as tablet or pocket personal computers ("PCs") 18. The NNA server 12 may also be connected with a plurality of remote terminals (e.g.—PC workstations) 20 through various types of network types that are operational to allow the server 12 and the remote terminals 20 to transmit and receive data between respective devices. The NNA system 10 may operate or function using various wired or wireless network setups and configurations.

Figure 2:
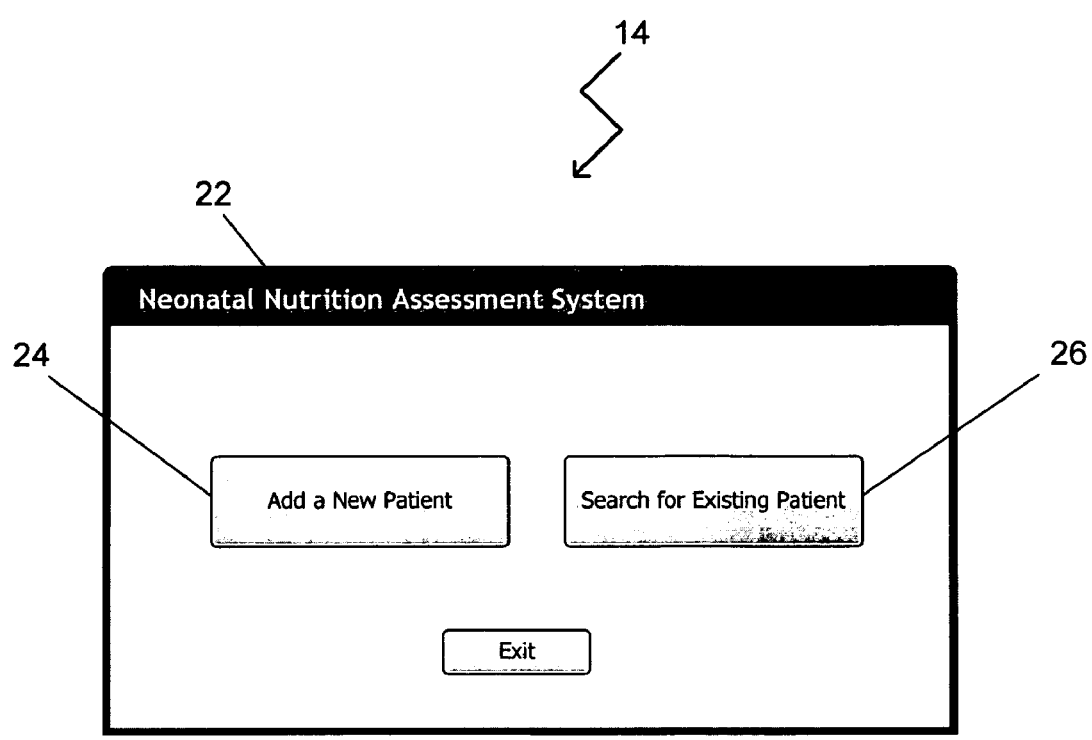
FIG. 2 represents an illustrative initial startup graphical user interface of the NNA software application.

Referring to FIG. 2, the NNA software application 14 may include a plurality of software modules that may run on the NNA server 12, the tablet PCs 18, the remote terminals 20 and/or a combination of all of the above. The NNA software application 14 may be designed as a "thin" or "fat" client. The NNA software application 14 may be developed to optimize the performance of the tablet PCs 18 and the remote terminals 20. As such, most of the data described below may be stored on the NNA server 12 and the calculations or processes performed by the NNA software application 14 may be performed by the NNA server 12 and the results may be "pushed" to the tablet PCs 12 or the remote terminals 20. The tablet PCs 18 and the remote terminals 20 are preferentially used to enter, edit, and view data that is generated and pushed to the tablet PCs 18 or remote terminals 20 from the NNA server 12.

Those skilled in the art of programming would recognize that various software modules may be distributed between the hardware devices used in the NNA system 10 to optimize performance. In the preferred embodiment, the NNA software application 14 is designed for use in conjunction with wireless tablet PCs 18 and as such, the discussion that follows will focus on the tablet PCs 18. However, it should be noted that all of the functionality described below may also be accomplished on the remote terminals 20 as well.

Once the NNA software application 14 is launched or started on the tablet PC 18 and the user has properly logged into the NNA system 10, the NNA software application 14 may generate an initial graphical user interface ("GUI") 22 that may provide access to an infant data input module 24 and an infant search module 26. The infant data input module 24 may allow the user to add a new patient record to the NNA system 10 or update daily records associated with the infant. The infant search module 26 may allow the user to search for an existing patient data record that is already entered and stored in the NNA system 10. As those skilled in the art would recognize, several different types of search fields may be used to search for a patient record.

When a user logs into the NNA software application 14 using a tablet PC 18 or a remote terminal 20, access rights to certain areas or functionality of the NNA software application 14 may be restricted on a user by user basis. For example, some individuals may only have "view only" access rights and other individuals may only have access to certain features and functionality. A physician or dietician (or other designated users) may have access rights to all of the features and functionality of the NNA software application 14 while nurses may only be able to enter data in appropriately designated fields, view reports and graphs. A nurse, intern or dietician, for example, may only be allowed to view a physician ordered script or patient diagnosis, but may not be allowed to modify or enter new scripts or diagnosis. In other hospital settings, a dietician and attending physician may be allowed to enter new nutritional scripts.

Referring back to FIG. 1, the NNA server 12 may also be connected with a pharmacy server 25, a lab server 27, and a hospital server 29. The pharmacy server 25 may allow a pharmacist to pull up and view ordered prescriptions that relate to infants in the NICU so that the pharmacist can fill the script while in other embodiments the pharmacist may be allowed to document scripts. Providing adequate and sufficient amounts of compatible nutrients to these patients is an extremely important part of caring for these patients. Modern formulas are standardized and may be modified and/or fortified to provide individualized and proper care to these special patients.

Although not specifically illustrated, the lab server 27 may include a laboratory software application that includes a database of patient lab test results. Most modern hospitals and/or NICUs may take advantage of commercially available laboratory test management software applications that have been specifically designed to keep track of lab test results. As set forth in greater detail below, the NNA software application 14 may provide patient lab results to caretakers and it is important for caretakers to have a clear understanding of the entire picture as it relates to the patient. Lab results may be used by caretakers for clinical evaluation and may result in modifications being made to the nutritional management of the patient. In one embodiment of the present invention, the NNA software application 14 may automatically query the lab server 27 once a patient record is selected to obtain the latest lab results that relate to that patient. In another embodiment, the lab results may be manually entered by a user of the NNA software application 14.

The hospital server 29 may include a general patient database that may contain demographic data about every patient in the hospital. Since NICUs are often separate or highly specialized parts of a hospital or infants are transferred to NICUs from other hospitals, the NNA software application 14 may have access to hospital server data files so that demographic data for a patient admitted to the NICU may be automatically populated based on previous data entries entered at the hospital. This allows NICU personnel to spend more time on caring for the infant and less time entering information about the infant that has already been entered.

Figure 3:
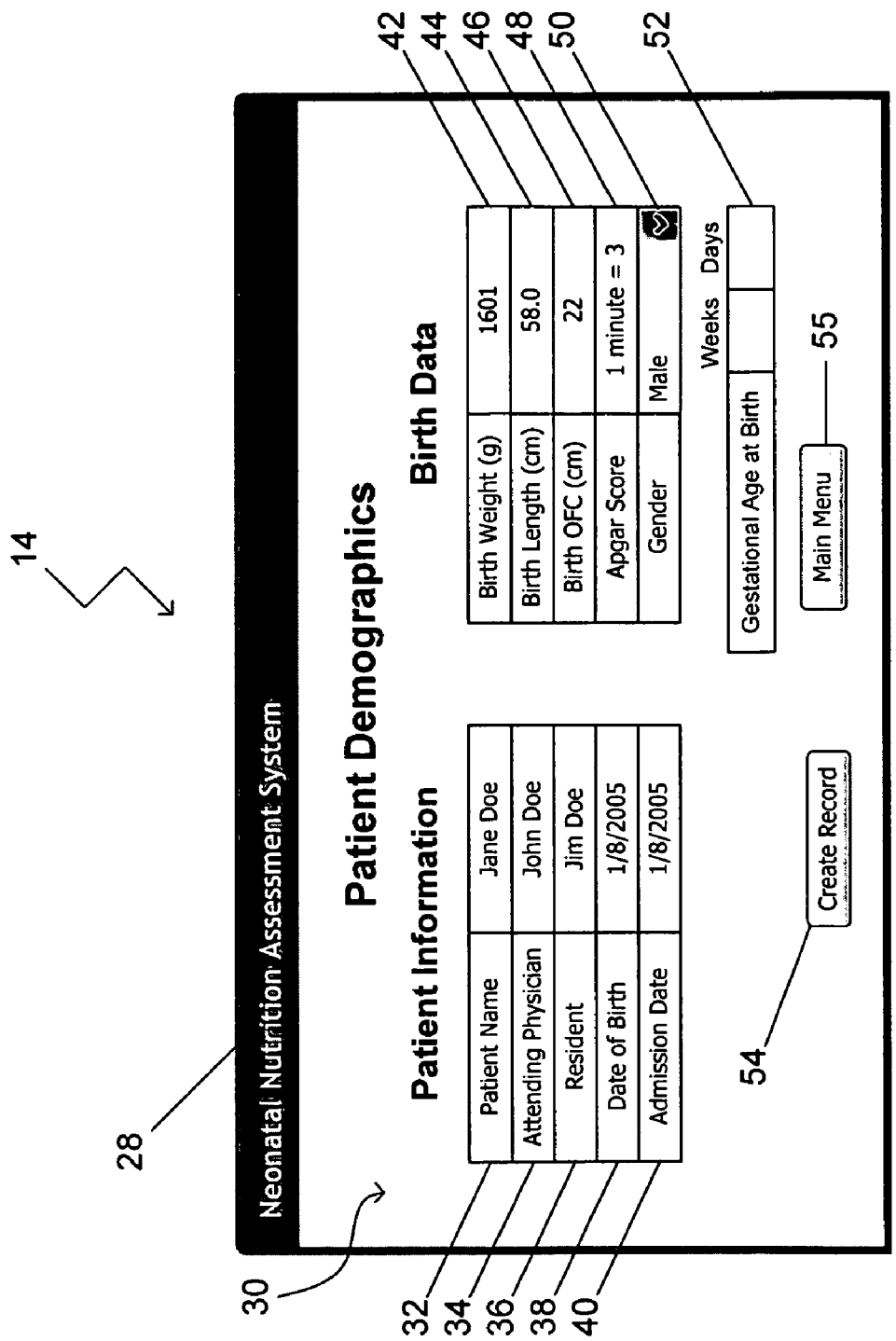
FIG. 3 represents an illustrative patient demographic graphical user interface of the NNA software application.

Referring to FIG. 3, an illustrative example of how a NICU staff member may create a patient record or demographic file is illustrated. If the user selects the infant data input module 22, the NNA software application 14 may generate a patient demographic GUI 28 on the tablet PC 18 that allows the user to enter, edit and view demographic data related to a patient. The patient demographic GUI 28 may include a plurality of demographic data fields 30. The demographic data fields 30 may include a name input field 32, an attending physician input field 34, a resident or resident team input field 36, a date of birth input field 38, an admission date input field 40, a birth weight input field 42, a birth length input field 44, a birth occipital frontal circumference ("OFC") input field 46, an Apgar score input field (e.g.—score at 1 minute, 5 minutes, and 10 minutes) 48, a gender input field (M/F) 50, and a gestational age at birth input field (weeks and days) 52. Data values for each of the above-referenced demographic fields 32-52 may be entered manually by the user of the NNA software application 14 through use of the tablet PCs 18 and the meaning of each demographic input field 32-52 is well known in the art. Once the data values have been entered in each respective demographic input field 32-52, the data may be stored in a patient database 53 (See FIG. 1) by selection of a create record command button 54. The patient database 53 may be physically stored on a separate server or may be stored on the NNA server 12. A main menu command button 55 may take the user to a main menu GUI 60 (see FIG. 4) for that particular patient.

Figure 4:
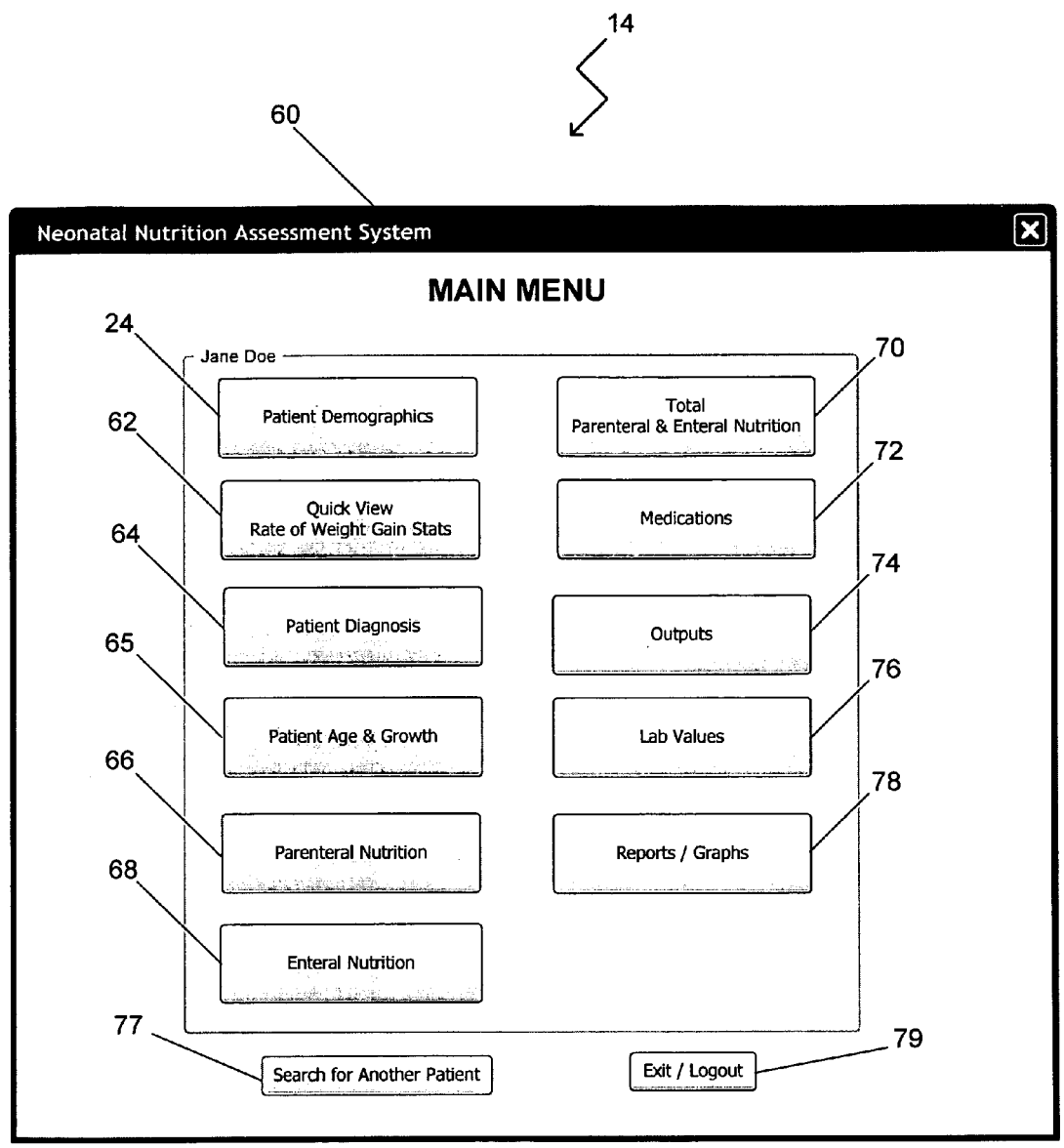
FIG. 4 represents an illustrative main menu graphical user interface of the NNA software application.

Referring back to FIG. 2, if the user selects the infant search module 26, although not illustrated, the user may be taken to a search GUI that allows the user to locate a given patient through the assistance of various search fields. These types of search screens or GUIs are well known in the art. Once the user locates the desired patient, a main menu GUI 60 may be generated by the NNA software application 14 on the tablet PC 18 for the selected infant, which is illustrated in FIG. 4. As such, the NNA system 10 allows users to add new patients and search for existing patients and the data associated with patients may be stored in and retrieved from the patient database 53.

Figure 5:
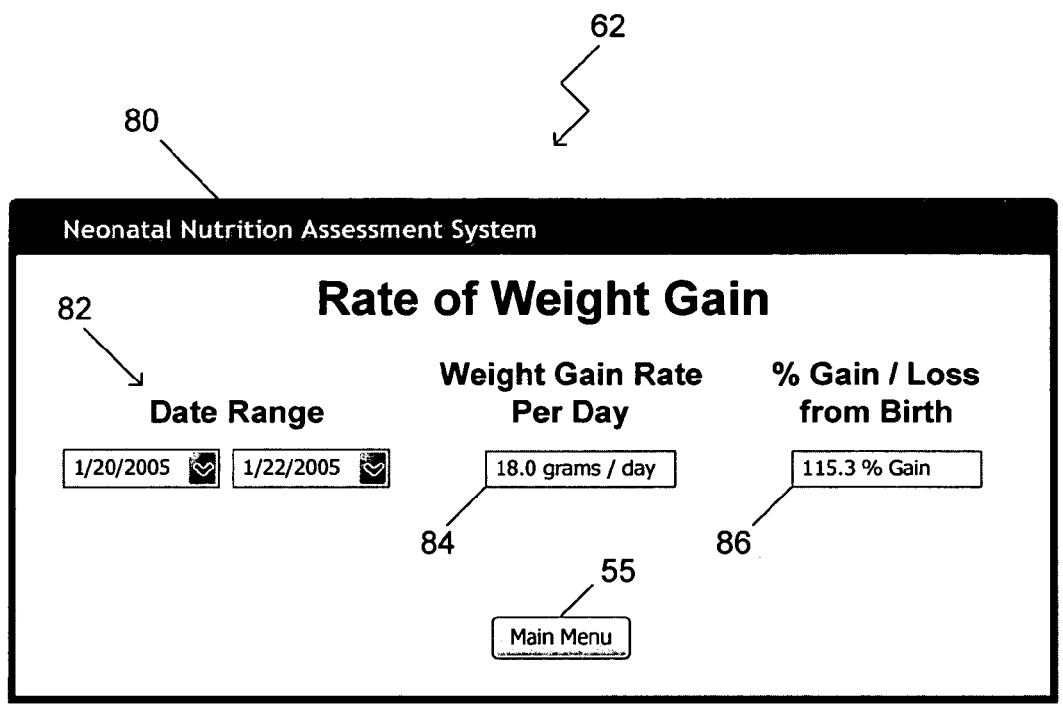
FIG. 5 represents an illustrative rate of weight gain graphical user interface of the NNA software application.

Referring to FIG. 4, the main menu GUI 60 may include access to the infant data input module 24. The user may select the infant data input module 24 to open a patient demographic GUI 28 (see e.g. FIG. 3) that is associated with the selected patient thereby allowing the user to enter, edit, or view demographic data associated with the patient for additional days, such as the infants weight. This allows the user to keep track of the infants weight on a daily basis, which as set forth below, is important for various calculations. The main menu GUI 60 may also include access to a rate of weight gain calculation module 62, a patient diagnosis module 64, a patient age and growth module 65, a parenteral nutrition module 66, an enteral nutrition module 68, a total parenteral and enteral nutrition module 70, a medications module 72, an outputs module 74, a lab value module 76 and a reports and graphs module 78. All of the above-referenced modules 24, 62-78 are illustrated as command buttons in the main menu GUI 60 and selection of a respective command button may cause the respective module to execute or load on the tablet PC 18. A new patient search command button 77 and an exit command button 79 may also be included in the main menu GUI 60, Referring to FIGS. 4 and 5, the rate of weight gain calculation module 62 is operable to allow the user to determine how much weight the infant has gained over a selected period of time or date range. Selection of the rate of weight gain calculation module 62 on the main menu GUI 60 may cause the NNA software application 14 to generate a rate of weight gain GUI 80 that may include a date range input field 82 that allows the user to enter a start date and an end date for the weight gain calculation. Once the date range is entered, the rate of weight gain calculation module 62 may automatically subtract the recorded infant weight at the starting date from the recorded infant weight at the ending date and then divide the result by the number of days indicated in the date range. For example, if the infant weighed 1,500 grams on the start date and 1,536 grams on the ending date and the date range is a two day period, the infant gained 18.0 grams per day. The rate of weight gain GUI 80 may include a weight gain rate output field 84, which may be automatically populated with the rate of weight gain over the chosen date range by the rate of weight gain calculation module 62. The rate of weight gain calculation module 62 may also calculate a percentage of weight gain or loss from birth and automatically populates a percentage of gain/loss field 86. As such, if a physician desires to quickly see how a prescribed feeding prescription is affecting the patient (i.e.—weight gain), they may quickly and easily view the results on the tablet PC 18. A main menu command button 55 may be included to return the user to the main menu GUI 60.

Figure 6:
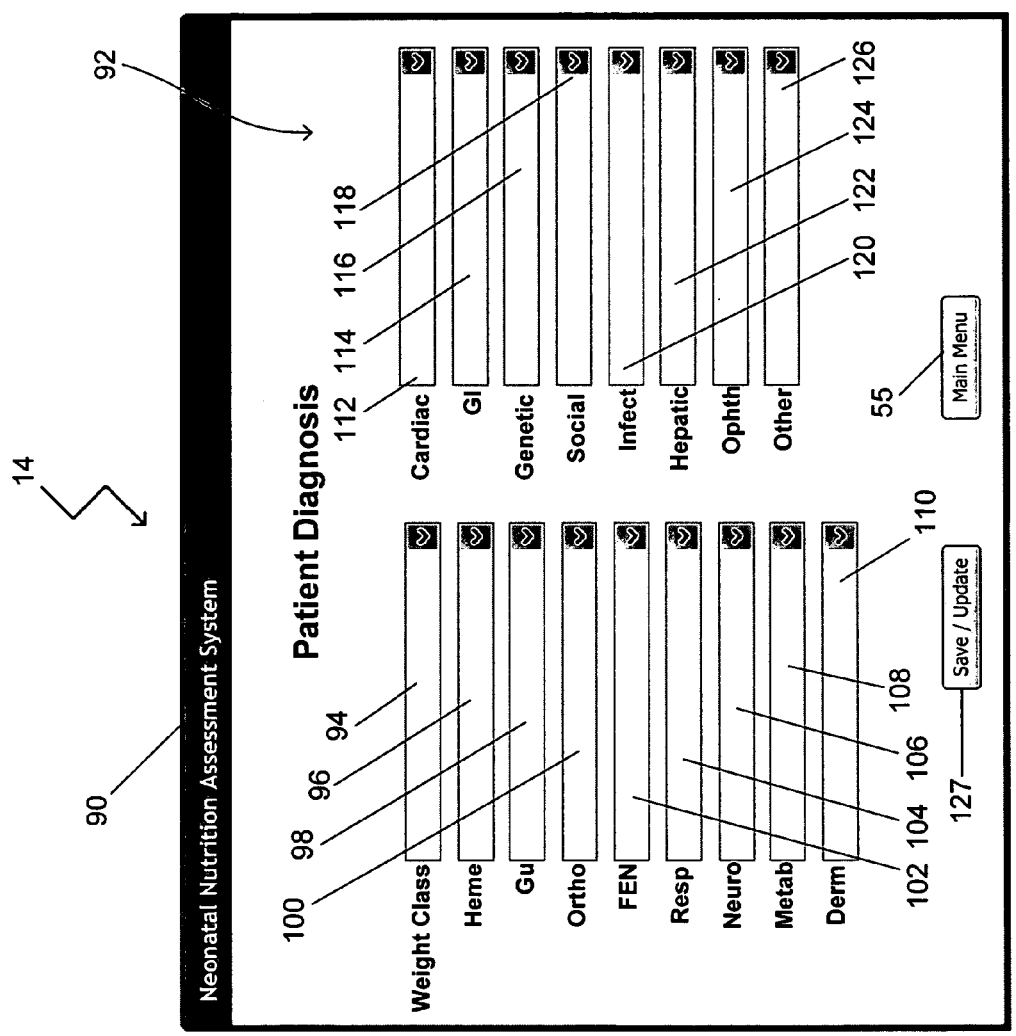
FIG. 6 represents an illustrative physician diagnosis graphical user interface of the NNA software application.

Referring to FIGS. 4 and 6, the patient diagnosis module 64 may allow a physician or caretaker to record medical conditions and/or ailments that are affecting the infant on any given day. The medical conditions and/or ailments may be entered and stored in the patient database 53 in a record file associated with that respective patient. Infants admitted to the NICU typically have one or more conditions that accompany the fact that the infant is premature with unique nutritional requirements. The patient diagnosis module 64 allows physicians to keep updated records relating to these conditions and provides an easy way for caretakers to lookup or view what diagnosis applies to each particular infant. Selection of the patient diagnosis module 64 in the main menu GUI 60 may cause the NNA software application 14 to generate a patient diagnosis GUI 90, which is illustrated in FIG. 6, on the tablet PC 18. The patient diagnosis assists dieticians screen for degrees of nutritional risks so that proper nutritional orders may be given for each respective patient.

The patient diagnosis GUI 90 may include a plurality of general categories of diagnosis 92 that allow a caretaker to record medical conditions and/or ailments that may be affecting the infant. The categories of diagnosis 92 may include a weight class category 94, a hematology ("Heme") category 96, a genital urinary ("GU") category 98, an orthopedic ("Ortho") category 100, a fluid, electrolyte and nutrition ("FEN") category 102, a respiratory ("Resp") category 104, a neurological ("Neuro") category 106, a metabolic ("Metab") category 108, a dermatology ("Derm") category 110, a cardiac category 112, a gastrointestinal ("GI") category 114, a genetic category 116, a social category 118, a infectious disease ("Infect") category 120, a hepatic storage ("Hepatic") category 122, an ophthalmology ("Ophth") category 124, and a miscellaneous or other category 126. Under each respective category of diagnosis 94-126, a plurality of medical conditions and/or ailments that fall within or under that category may be stored in a drop down list. The categories of diagnosis 92 are represented as drop down lists in which the user may select the appropriate diagnosis from a list that is generated when the appropriate category selection box is selected. Various types of diagnosis options under each category may be stored in and retrieved from the database 53, which may be updated from time to time as needed. Although drop down lists are illustrated in this embodiment, various other methods of allowing a caretaker to record medical conditions and/or ailments may exist.

As illustrated in FIG. 6, a Save/Update button 127 may be included in the patient diagnosis GUI 90. The Save/Update button 127, when selected by the user, may cause the NNA software application 14 to save the values entered in the patient diagnosis GUI 90 to a database file associated with the patient in the database 53. For the purpose of the present invention it is important to note that the NNA software application 14 is capable of storing various data values, as disclosed herein, that are associated with individual patients. As such, each patient will have a patient record that is stored in the patient database 53. The patient records may be updated on various timetables as required for each individual patient.

The patient diagnosis GUI 90 may also include a Main Menu button 55 that, when selected, will cause the NNA software application 14 to return the user to the Main Menu GUI 60 for the patient. For the sake of brevity, the Save/Update button 127 and the Main Menu button 55 may be included in various GUIs disclosed herein. However, a detailed description of the functionality of these respective buttons 127, 55 for each GUI will not be set forth as the functionality essentially remains the same throughout the various GUIs (i.e.—to either save or update patient records in the patient database 53 or return the user to the Main Menu GUI 60).

Figure 7:
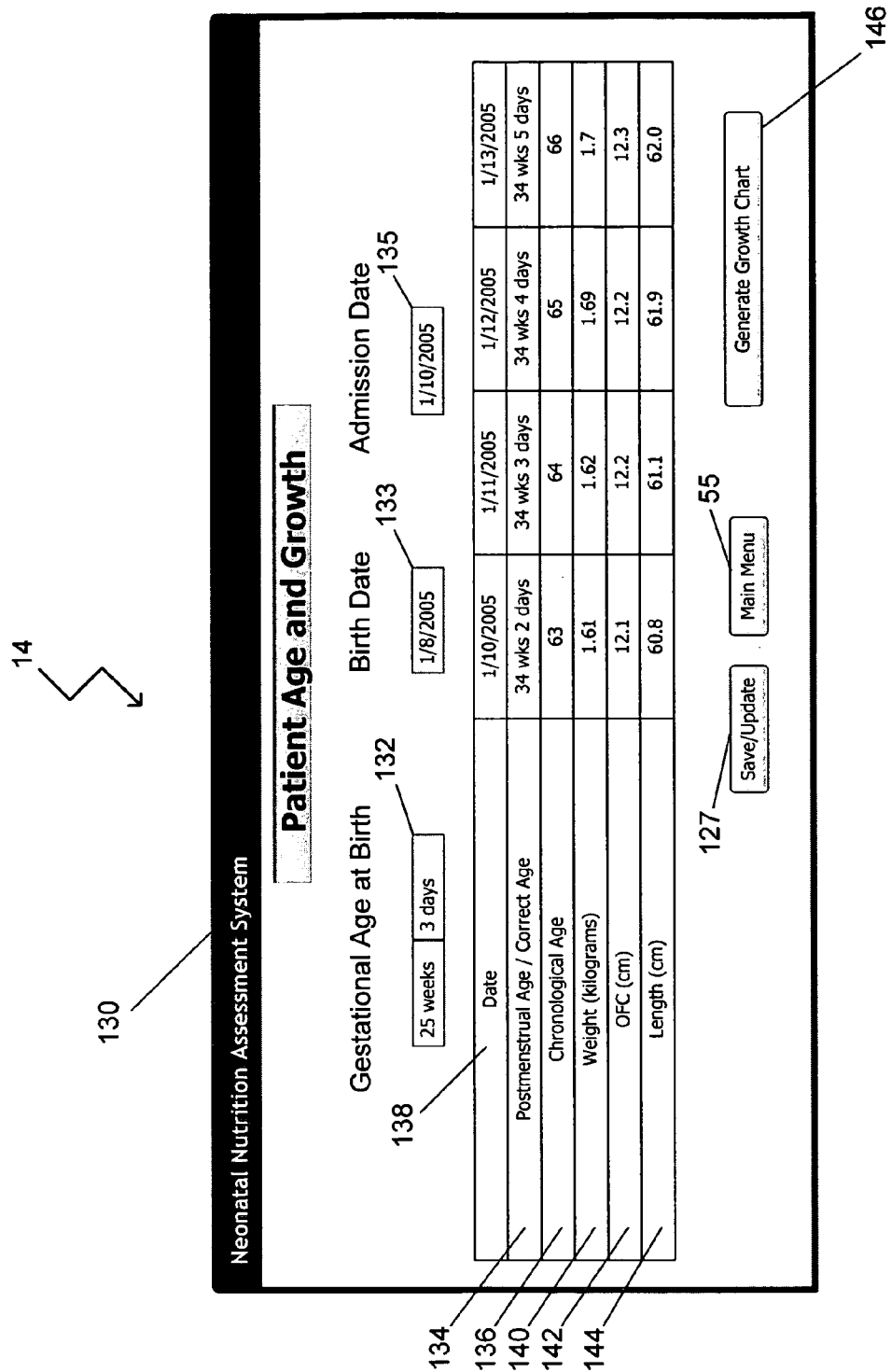
FIG. 7 represents an illustrative patient age and growth graphical user interface of the NNA software application.

Referring to FIGS. 4 and 7, selection of the patient age and growth module 65 may cause the NNA software application 14 to generate a patient age and growth GUI 130 on the tablet PC 18. The patient age and growth GUI 130 may include a gestational age at birth display field 132 that represents a data value that may have been entered using the patient demographics GUI 28. The data value present in the gestational age at birth display field 132 represents the gestational age of the child at birth. Refer to the discussion of FIG. 3 for a discussion of some of the data values present in the patient age and growth GUI 130. The patient age and growth GUI 130 may also include postmenstrual age display fields 134 and chronological age display fields 136, which are fields that are automatically calculated and populated by date by the NNA software application 14. The chronological age is calculated as: today's date minus birth date. The postmenstrual age is calculated as: current gestational age (current age in weeks and days) plus gestational age at birth.

As illustrated in FIG. 7, the patient age and growth GUI 130 may be generated as a table that includes a plurality of columns 138 that contain data values based on dates (e.g.—days of the month). The patient age and growth GUI 130 may also include a patient birth date display field 133 and a patient admission date display field 135. The patient birth date display field 133 is used to display the actual date that the infant was born. The patient admission date display field 135 is used to display the date that the infant was admitted to the NICU.

As further illustrated in FIG. 7, the patient age and growth GUI 130 may also include a weight input field 140 for each day. The weight field 140 may be entered by a care provider after the infant is weighed each day. The patient age and growth GUI 130 may also include an OFC input field 142. The OFC field 142 may also be entered by a care provider after each time it is measured. The patient age and growth GUI 130 may also include a length input field 144 that is used to record the length of the infant each day. The patient age and growth module 65 may also include a growth chart module 146 that is operable to generate a growth chart for the infant based on the infant's weight measurements, OFC measurements, and length measurements (see FIGS. 19, 20, 21). The exact look and feel of the growth chart may vary depending upon the needs of the user of the NNA system 10 as well as the display limitations of the tablet PC 18.

Referring to FIGS. 4 and 8, selection of the parenteral nutrition module 66 in the main menu GUI 60 may cause the NNA software application 14 to generate a daily pediatric parenteral nutrition order GUI 150 on the pocket PC 18. Parenteral nutrition refers to the supplemental intravenous infusion of nutrients by peripheral or central vein. Infants in NICUs may not be able to breastfeed or take a bottle and often must be nourished through parenteral nutrition. As a result, a special liquid preparation or script is ordered and prepared that is referred to as parenteral hyperalimentation. The NNA software application 14 allows a physician or dietician to specifically enter an order for a parenteral hyperalimentation mixture that will be given to the infant and to keep track of what was given to the infant during each feeding.

The nutritional makeup of the hyperalimentation solution that is prepared for an infant based on physician or dietician orders is critical to the growth and development of infants in the NICU. The orders may be filled by a pharmacy that is located within the hospital or by other means. The pharmacy may have access to certain portions of the NNA software application 14 for the purpose of filling these orders. Or, in the alternative, orders may be printed out and sent to the pharmacy for each patient.

The daily pediatric parenteral nutrition order GUI 150 provides physicians and dieticians with a valuable tool that allows them to easily prescribe fluids to be given the infant through parenteral nutrition. All babies need nutrition in order to properly develop, but ensuring that babies are receiving proper amounts of calories, protein, and fats is extremely important. The daily pediatric nutrition order GUI 150 allows physicians to carefully control the amount and rate at which infants receive fluids, electrolytes, vitamins and other nutrients and micronutrients. The hyperalimentation solution may be given as one or more mixtures or bags during any given day or over any predetermined time period.

The daily pediatric parenteral nutrition order GUI 150 may include a parenteral nutrition entry field 152. The parenteral nutrition entry field 152 includes a plurality of manual data entry fields. A check box 154 may be used for standardized order fields and a numeric field 156 may be used for individualized quantitative orders. The daily pediatric parenteral nutrition order GUI 150 allows users to view prior parenteral nutrition orders and to make new orders for any given day or feeding period. The parenteral nutrition orders made for each patient may be stored in the patient database 53 in a file or record associated with the patient.

As illustrated, the parenteral nutrition entry field 152 may be broken down in a plurality of columns 158, which may be representative of dates or predetermined time periods. The parenteral nutrition entry field 152 may include a central ("Cen") data input field 160, a peripheral ("Per") data input field 162, a sodium ("Na") data input field 164, a potassium ("K") data input field 166, a chloride ("Cl") data input field 168, a phosphorus ("P") data input field 170, a calcium ("Ca") data input field 172, a magnesium ("Mg") data input field 174, a multivitamin ("MVI") data input field 176, a trace mineral ("TES") data input field 178, a zinc ("Zn") data input field 180, a ranitidine ("Ranite") data input field 182, a carnitine ("Carn") data input field 184, a heparin ("Hep") data input field 186, and an other data input field 188. The central data input field 160 and the peripheral data input field 162 relate to the manner in which the hyperalimentation solution is delivered to the patient. Typically, only one of these boxes will be checked as normally only one delivery method would be used. The meanings of the nutrient fields are understood as it relates to this subspecialty and as a result, a detailed explanation of these fields is not required.

The daily pediatric parenteral nutrition order GUI 150 may include a parenteral nutrition ("PN") dosing weight data input field 190. The PN dosing weight relates to the patient's estimated dry weight expressed in kilograms that parenteral nutrition is calculated on. A time data input field 192 may be included that is determinative of the number of hours to be used in calculating the PN dosing weight. An order infusion rate data input field 194 may also be included that is a manually entered data field that is obtained from the pharmacy script. The order infusion rate data input field 194 may be entered in a volume quantity (e.g.—mL/hour).

A physician ordered infusion rate data input field 196 may also be included that may be manually entered by a physician. This is the infusion rate ordered by the physician, which can be different from what is contained in the pharmacy script. The physician order infusion rate data input field 196 may also include an automatically calculated display of a percentage of the physician prescription as it relates to the order infusion rate (i.e.—(Physician Order Rate/Order Infusion Rate)×100=% RX Script). The daily pediatric nutrition order GUI 150 may also include a volume data field 198, which is automatically calculated by the NNA software application 14. The value displayed in the volume data field 198 is calculated as follows: ((Order Infusion Rate×Hours to be used in rate calculation/PN Dosing Weight)=Volume of Script (mL/kg)).

Figure 9:
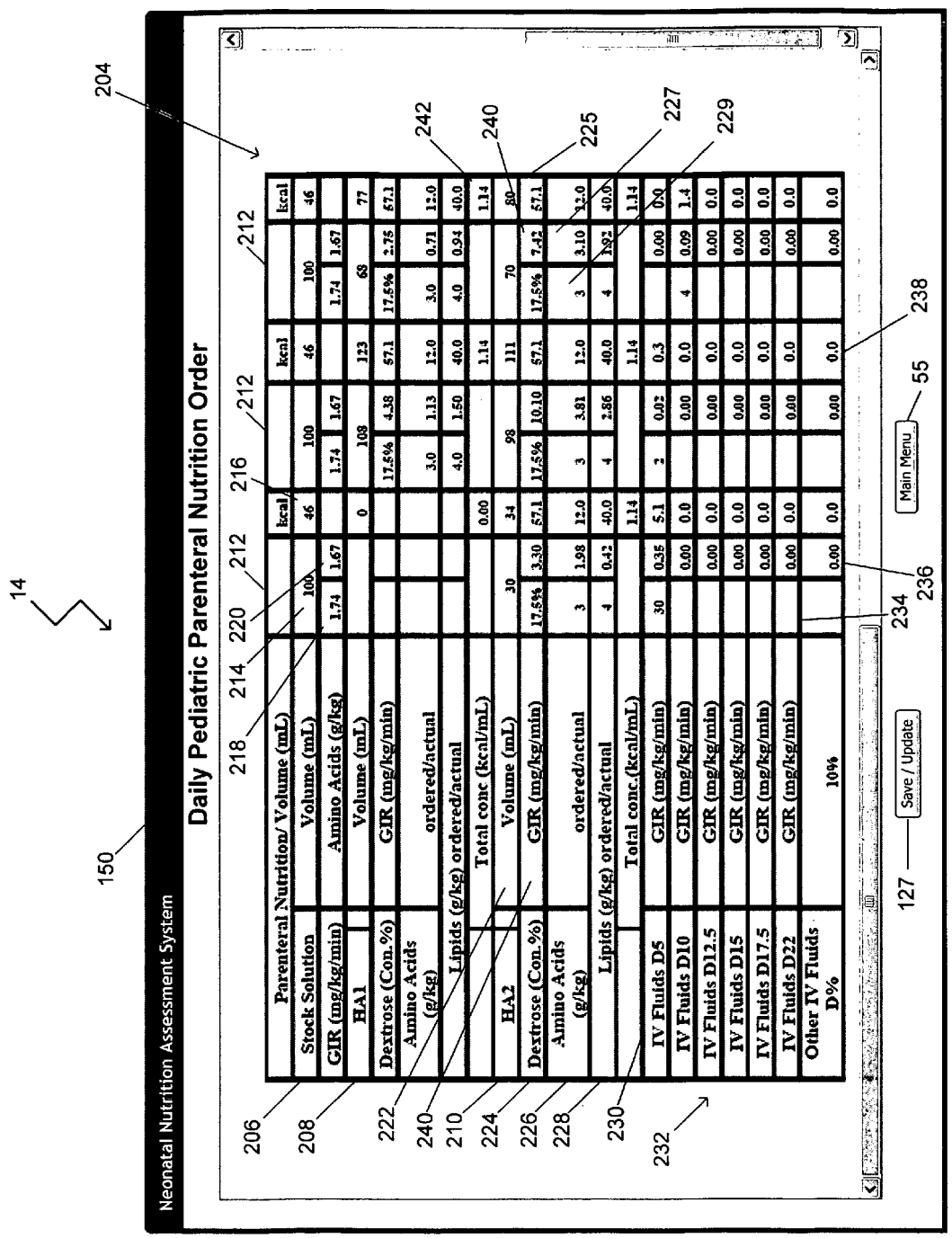
FIG. 9 represents additional fields that may be displayed in the parenteral nutrition order graphical user interface of the NNA software application.

Referring to FIG. 9, the daily pediatric parenteral nutrition order GUI 150 may also include additional fields. The daily pediatric parenteral nutrition order GUI 150 may also include a parenteral nutrition volume display 204, which may allow the user to select one or more different types of hyperalimentation solutions. As set forth in greater detail below, the NNA software application 14 is operable to automatically calculate the calorie density from dextrose, amino acids and lipids as well as the overall total calorie intake. The NNA software application 14 is also operable to automatically calculate the glucose infusion rate, which is dependent upon the total dextrose concentration.

The first type may be referred to as a Stock Solution 206, the second type may be referred to as a First Hyperalimentation solution ("HA1") 208 and the third type may be referred to as a Second Hyperalimentation solution ("HA2") 210. The Stock Solution 206 is often given to infants the first few days after birth. After examination by a physician, the physician may issue a script for a custom hyperalimentation solution that is specific to the infant's needs, which correlates to the HA1 208 and the HA2 210. As illustrated in FIG. 9, the data fields of the parenteral nutrition volume display 204 may be divided up into eight (8) hour time frames 212, but other time frames may be used as well.

The Stock Solution 206 may include a volume input field 214, which is a manually entered data field in which a user calculates a numeric value, preferentially in milliliters, for the volume of stock solution that has been provided to the infant over a predetermined period of time (e.g.—24 hour intervals). Based on the value entered in the volume input field 214, the NNA software application 14 automatically calculates the amount of calories received through parenteral nutrition and displays the result in a calorie display field 216. For a standard stock solution (e.g.—Dextrose at 7.5%, Amino Acids at 3.0 g/kg, Lipids 0 g/kg and Volume 60 mL/kg), the calorie content of the solution is 0.46 kcal/mL. As such, the calorie content of the stock solution may be calculated as: kcal/mL×mL=kcal.

The Stock Solution 206, and all parenteral nutrition fluids, may also include a glucose infusion rate ("GIR") field 218. The GIR field 218 may be automatically calculated by the NNA software application 14. The data value placed in the GIR field 218 may be calculated by using the following equation: GIR=g/kg/day dextrose×1000=mg/kg/day/1440 min/day=mg/kg/min glucose. Monitoring the GIR is important because hypoglycemia can occur if the solution containing dextrose is abruptly stopped. Hyperglycemia may also occur and may be caused by decreased insulin production or insulin resistance, increased heptatic glucose production, or other causes.

The Stock Solution 206 may also include an amino acids field 220, which may also be automatically calculated by the NNA software application 14 based on the volume of stock solution delivered to the patient as well as the nutrients or contents of the stock solution. Amino acids are the basic structural units of proteins and may be measured in grams of protein per kilogram (grams of protein/kg). Proteins are essential to the structure and function of all living cells. Some proteins play structural or mechanical roles, such as those that form the struts and joints of the cytoskeleton, serving as biological scaffolds for the mechanical integrity and tissue signaling functions. Still more functions filled by proteins include immune response and the storage and transport of various ligands. In nutrition, proteins serve as the source of amino acids for organisms that do not synthesize those amino acids natively and are important for proper growth and development.

In a typical NICU environment, during rounds the physician will determine the nutritional needs of each infant. The physician will make a determination on whether or not to change the script, and if so, will enter a new script into the NNA software application 14. Once the script is filled by the pharmacy, it is delivered to the NICU where parenteral feeding is started, which may occur, for example, during the evening between 18:30 to 6:29 (assuming a 24 hour timetable is used). The HA2 solution 210 may be ran from about 18:30 to 6:29. The HA2 solution 210 typically is a nutrient solution that may comprise three (3) components: dextrose, amino acids, and lipids. The HA1 solution 208, which is typically the same solution as the HA2 solution 210, may be administered from 6:30 to 18:29. As set forth above in relation to FIG. 8, it is important to note that the scripts that are issued by the physician and recorded by the NNA software application 14 in the patient database 53 are typically custom written for each infant each day. Other timetables may be used in the present invention.

The HA2 solution 210 may have a plurality of data entry fields that require user input, which may include a HA2 volume input field 222, a dextrose concentration input field 224, an HA2 amino acids input field 226, a lipids input field 228, and possibly at least one intravenous ("IV") fluids volume input field 230. The HA2 volume input field 222 is the volume amount, preferentially given in milliliters, which the script is written for by the physician as it relates to the HA2 solution 210. As set forth above, the HA2 solution 210 may comprise three components: dextrose, amino acids, and lipids. The calorie display field 216 may be used to display the total amount of calories provided by the HA2 solution 210 as well as the amount of calories delivered or consumed by the patient. Calories from the HA2 solution 210 may be calculated by multiplying the HA2 volume intake by the caloric density of the HA2 solution 210. The results of this calculation may be automatically displayed by the NNA software application 14 in the calorie display field 216.

The dextrose concentration input field 224 allows the user to enter a value indicative of the concentration of the dextrose used in the HA2 solution 210. Dextrose is commonly used as a source of rapidly absorbed energy, a carrier in water soluble medications, and may come in different strengths or concentrations, which may be calculated as a percentage value. The dextrose concentration input field 224 may include a dextrose calorie concentration field 225, the data value of which, is automatically calculated and displayed by the NNA software application 14. The data value in the dextrose calorie concentration field 225 may be calculated by multiplying the amount of kilocalories per milliliter of the dextrose solution by the dextrose concentration per milliliter and then multiplying that result times the volume entered in the HA2 volume field 222 ((Dextrose concentration times the number of kilocalories per milliliter)×Volume mL/kg).

The HA2 amino acids field 226 relates to the amount of calories the physician desires the infant to receive through the HA2 solution 210 by way of amino acids. The HA2 amino acids field 226 may include an ordered amino acids data input field 227 that allows the physician to designate a numeric amount of amino acids ordered (e.g.—3 g/kg) and an actual amino acids field 229 that is automatically calculated as a function of the volume of the HA2 solution 210 that is actually delivered to the patient. The calorie display field 216 may be used to display the total amount of calories the patient received over a given time period through amino acids (e.g. Calories=((Amino Acids g/kg*10 mL)*0.4 kcal/mL)*Volume mL/kg)).

The lipids field 228 relates to the amount of calories the physician desires the infant to receive through the HA2 solution 210 by way of lipids. Lipids are biological molecules that are insoluble in aqueous solutions and soluble in organic solvents. They serve as structural components of biological membranes, provide energy reserves, and serve as vitamins and hormones. As illustrated, the HA2 lipids field 228 may include an ordered lipid data field that allows the physician to designate or enter a numeric amount of lipids ordered (e.g.—2 g/kg) and an actual data field that is automatically calculated as a function of the volume of the HA2 solution 210 that is delivered to the patient. The calorie display field 216 may be used to display the total amount of calories the patient received over a given time period through lipids delivered via the HA2 solution 210 (e.g. (10% lipids) Calories= (lipids g/kg ordered*10 mL/g*1.1 kcal/mL).

The IV fluids volume field 230 may allow a physician to prescribe a plurality of different IV fluids to the patient. The IV fluids volume field 230 may include a list of a plurality of IV fluids 232 that may be prescribed to the patient. The IV fluids volume field 230 may include an ordered data entry field 234 and an IV calorie display field 236. The ordered data entry field 234 is used by the physician to order the amount of IV fluids the patient should receive and the IV calorie display field 236 displays the amount of calories the patient received from the IV fluid. An IV GIR display field 238 is included and the data values displayed in the IV GIR data field 238 are automatically calculated and populated by the NNA software application 14 (e.g. IV GIR=(((D5 volume/PN dosing weight)*0.05)/1.440).

The total GIR may also be automatically calculated by the NNA software application 14 as it relates to the HA2 solution 210. A total GIR display field 240 may be included to display the total GIR. The total daily GIR may be calculated using the following equation: Total Daily GIR=(((HA2 volume mL/PN Dosing weight)*Dextrose percentage)/min per day)+(Stock Solution GIR+HA1 GIR). The NNA software application 14 may also automatically calculate the HA2 total caloric density. The HA2 total caloric density may be displayed in an HA2 caloric density display field 242. This value is calculated as the sum of calories from dextrose, amino acids, and lipids all per g/kg, divided by the volume/kg of the same day. A detailed discussion of the HA1 solution 208 is not necessary as the inputs and outputs associated with the HA1 solution 208 are similar to the discussion relating to the HA2 solution 210 and as such, a detailed discussion of the HA1 solution and its associated data and input values are not necessary.

Referring to FIG. 10, the daily pediatric parenteral nutrition order GUI 150 may include a total parenteral nutrition display 250. The total parenteral nutrition display 250 may display data values for a given patient in time period columns 252. The total parenteral nutrition display 250 may include a total parenteral nutrition volume display field 254, which represents the total volume amount of parenteral nutrition from all sources provided to the patient for a given day. The value displayed in the total parenteral nutrition volume display field 254 is automatically generated by the NNA software application 14 as a function of the total amount of Stock Solution 206, HA1 solution 206, and HA2 solution 208 provided to the infant.

The total parenteral nutrition display 250 may also include a total parenteral nutrition per body weight display field 256. The NNA software application 14 automatically calculates a value for the total parenteral nutrition per body weight display field 256 by dividing the value set forth in the total parenteral nutrition volume display field 254 by the value entered in the weight field 140 (see FIG. 7) for that given day or select period of time. The weight of infants in the NICU is typically taken at least once a day and may be recorded in kilograms or any other form of weight measurement. The total parenteral nutrition display 250 may also include a total parenteral nutrition per dosing weight display field 258. The NNA software application 14 automatically calculates the value placed in this field by taking the value in the total parenteral nutrition volume display field 254 and dividing it by the value entered in the parenteral nutrition dosing weight field 190 (see FIG. 8) for that given day.

A total parenteral nutrition calorie display field 260 may also be included for displaying the total amount of calories the infant received from all parenteral nutrition sources (e.g.—Stock Solution 206+HA1 Solution 208+HA2 Solution 210+IV Fluids 232). This value may also automatically be calculated by the NNA software application 14 by adding all the calorie data values calculated with respect to each of the solutions provided to the infant. A total parenteral nutrition per unit by actual body weight field 262 may also be included for displaying the total amount of calories received per unit body weight. This value may also automatically be calculated by the NNA software application 14 by dividing the value contained in the total parenteral nutrition calorie display field 260 by the value entered in the weight field 140 for that given day or a select period of time.

The total parenteral nutrition display 250 may also include a total parenteral calories by dosing weight field 264. The NNA software application 14 automatically calculates the value placed in this field by taking the value in the total calorie display field 260 and dividing it by the value entered in the parenteral nutrition dosing weight input field 190 for that given day. A total projected parenteral nutrition volume input field 266 that is operable to receive an input value from a user relating to a projected volume value. The NNA software application 14 will use the data value placed in the projected parenteral nutrition volume input field 266 to calculate a total projected parenteral nutrition calorie delivery that is automatically displayed in a total projected parenteral nutrition calorie requirement display field 268. The total projected parenteral nutrition calorie requirement may be calculated by multiplying the value entered in the total projected parenteral nutrition volume input field 266 by the calorie content of the solutions being provided the patient.

The daily pediatric parenteral nutrition order GUI 150 may also include a protein calculation tool 270. The protein calculation tool 270 may include a total parenteral nutrition protein display field 272 that will automatically display the total actual delivered protein over a predetermined time period or number of days through parenteral nutrition. The protein calculation tool 270 may also allow a user to calculate the average parenteral nutrition protein received by the patient over a given number of days. A number of days input field 274 is included that allows a user to enter the number of days to be included in the calculation. A start date input field 276 is also included that allows the user to enter a starting date for the calculation. Once these values are entered, the protein calculation tool 270 automatically calculates the average parenteral nutrition protein received over the given time period and displays it in an average protein display field 278. The protein calculation tool 270 may also include a NPC: N Ratio calculation display field 280. This relates to the amount of calories that are received by the infant through non-protein sources relative to grams of nitrogen. The protein calculation tool 270 may calculate this value for a given day by using formulas known in the art.

Figure 11:
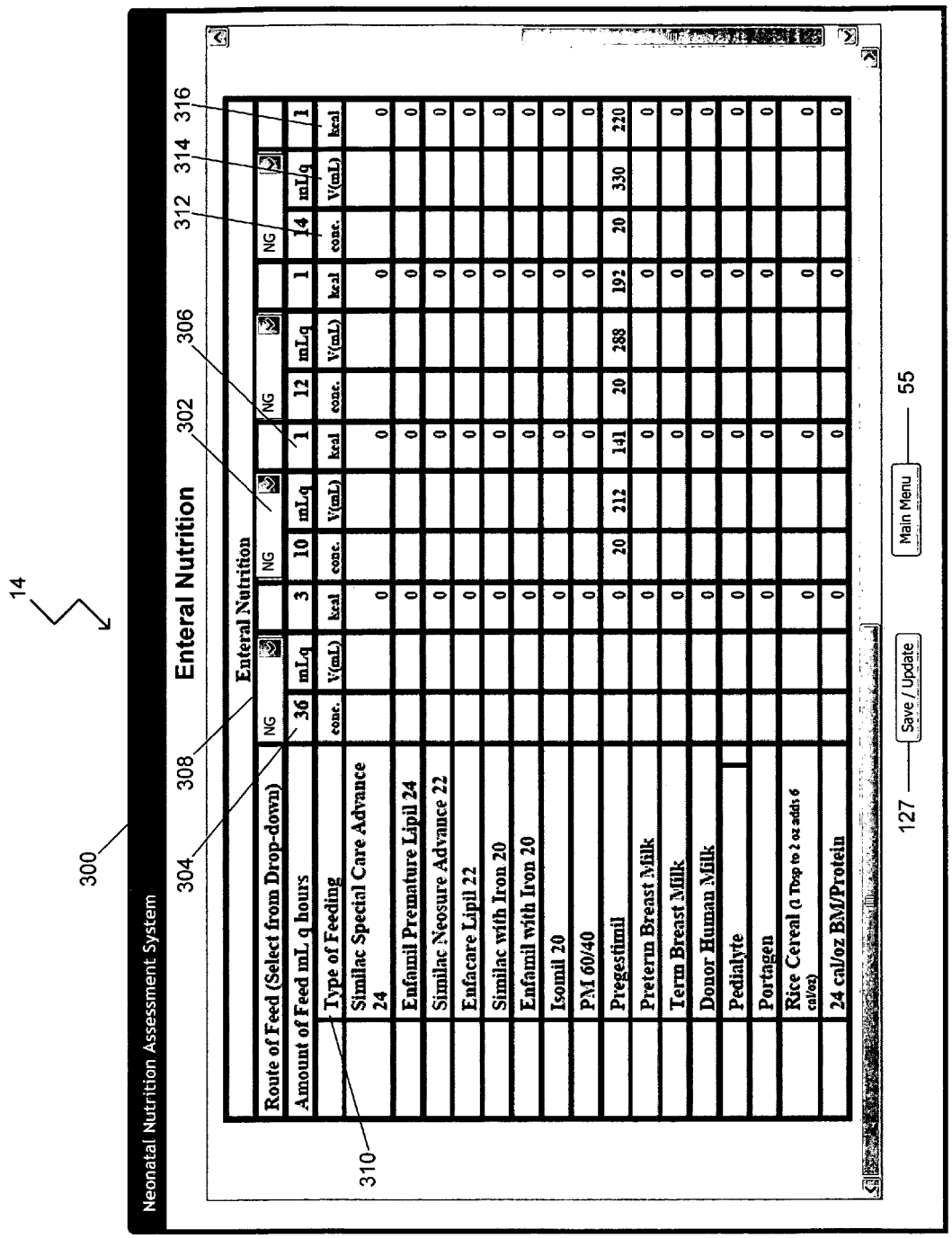
FIG. 11 represents an illustrative enteral nutrition graphical user interface of the NNA software application.

Referring to FIG. 4, the main menu GUI 60 may also include the enteral nutrition module 68. Selection of the enteral nutrition module 68 by the user may cause the NNA software application 14 to automatically bring up an enteral nutrition GUI 300, which is illustrated in FIG. 11. Enteral nutrition is provided by oral or gavage feedings. In such cases, the only alternative to enteral nutrition is, as set forth above, parenteral nutrition or intravenous nourishment. This is not usually a good long-term solution because the intravenous solution, with its amino acids and vitamins, provides a rich medium in which bacteria can grow and infect the bloodstream. Enteral feeding is usually the best long-term solution unless the child has a problem with nutrient absorption, severe chronic diarrhea, severe inflammatory bowel disease or another condition that makes enteral feeding impractical.

The enteral nutrition GUI 300 may include a feeding route selection 302 that the user uses to select the method in which the infant will receive enteral nutrition. The feeding route selection may be made using a drop down menu. The feeding route selection 302 may include a nothing by mouth ("NPO") option, a nasojeujenum ("NJ") option, a by mouth ("PO") option, an orogastric tube ("OG") option, a nasogastric tube ("NG") option and a gastrostomy tube ("GT") option. The enteral nutrition GUI 300 may also include a feeding amount input field 304 and a time input field 306. The feeding amount input field 304 may be a manual data input field that allows the user to enter the amount or volume of fluid to be fed to the infant. The time input field 306 is used to designate the amount of time over which the infant should be fed (e.g.—30 mL over 3 hours). As with the other embodiments, the enteral nutrition GUI 300 may contain data broken down into columns 308 that represent set periods of time (e.g.—hours, days, etc.).

The enteral nutrition GUI 300 may also include a type of feeding display field 310. The type of feeding display field 310 relates to the type of formula that may be used to make up the solution given to the infant. As illustrated, the infant may be given fluid made using various types of formula provided from various formula suppliers, different types of breast milk, rice cereal and so forth. To the right of each fluid type are three data fields for each respective day. The first data field is a concentration data input field 312, which allows the user to designate the concentration of the formula used in the fluid fed to the infant. The second field is a fluid volume data input field 314, which allows the user to designate the volume of that specific type of fluid to be fed to the infant. The third field is a calorie display field 316, which displays the total calories contained in the volume of fluid and is automatically calculated by the NNA software application 14.

Although not specifically illustrated, the database 53 may store a plurality of data values associated with the nutritional contents of each type of fluid contained in the type of feeding display field 310. The NNA software application 14 is operable to automatically calculate and display the total calories contained in the fluid using the data values stored in the database 53 for each type of formula or fluid, together with the volume entered in the fluid volume data input field 314 and the concentration data input field 312. As such, the user can quickly and easily ensure that the calorie content of the fluid is proper for any given patient.

Figure 12:
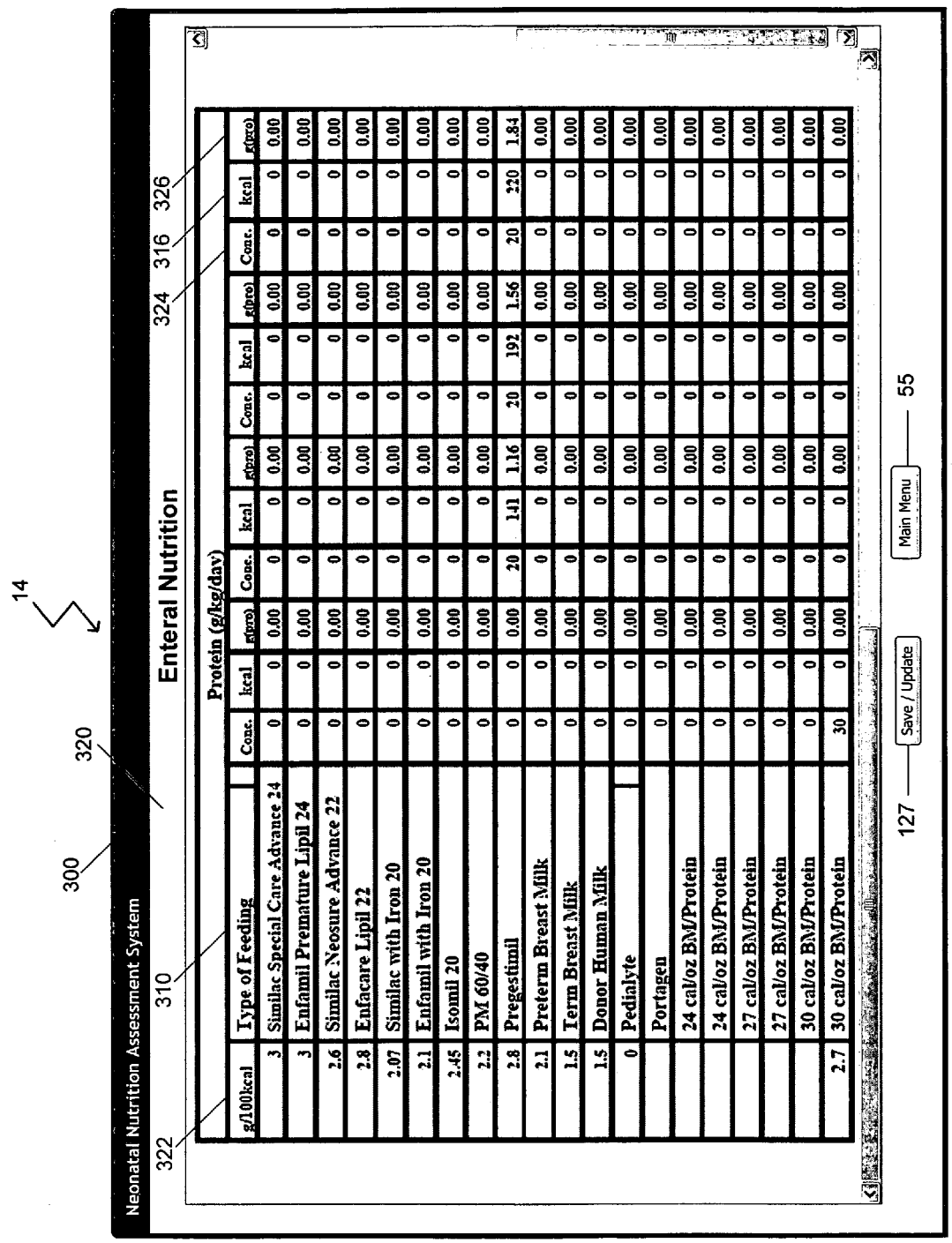
FIG. 12 represents an illustrative enteral nutrition protein calculation graphical user interface of the NNA software application.

Referring to FIG. 12, the enteral nutrition GUI 300 may also include an enteral nutrition protein calculation module 320. The protein calculation module 320 uses the information entered by the user set forth in FIG. 11 as well as the total calorie value to calculate the amount of protein the infant receives from enteral nutrition sources. The type of feeding field 310 automatically populates based on the user selections from FIG. 11. As such, selecting Similac Special Care Advance 24 in FIG. 11, will automatically tell the NNA software application 14 to populate fields associated with this formula in the enteral nutrition protein calculation module 320.

A grams of protein per kilocalorie and/or kilogram display field 322 may be included that displays the amount of grams per 100 kilocalories (other numeric values may be used), which is populated automatically by the protein calculation module 320 for the selected formula. The protein calculation module 320 may retrieve this information from the database 53. A concentration display field 324 may also be included that is populated automatically based on the input received in the concentration data input field 312. The total calorie display field 316 contains the same value as calculated in relation to the discussion of FIG. 11. The protein calculation module 320 uses the value contained in the grams of protein per kilocalorie and/or kilogram display field 322, the concentration display field 312, and the total calorie display field 316 to automatically calculate a total protein value, which may be displayed in a total protein display field 326. In alternative embodiments of the present invention, each formula does not need to be listed and only the formula used on each day may be listed. Although not illustrated, various other nutrient data calculations may be presented to the user in addition to a protein total, such as a sodium display, a calcium display, a phosphorus display and so forth.

Figure 13:
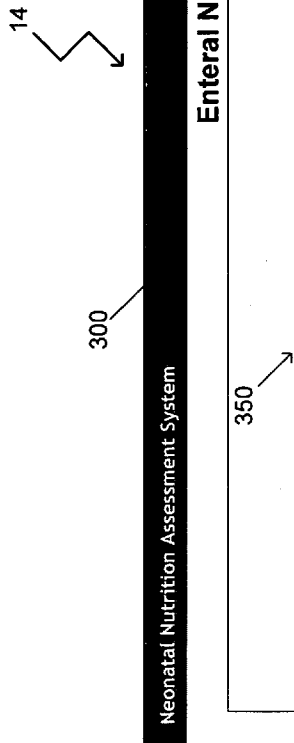
FIG. 13 represents an illustrative total enteral nutrition graphical user interface of the NNA software application.

Referring to FIG. 13, the enteral nutrition GUI 300 may also include a total enteral nutrition module 350. The total enteral nutrition module 350 automatically calculates and displays various data values relating to the enteral nutrition intake of the infant. The total enteral nutrition module 350 may include a total PO volume and percentage PO display field 352. The total PO volume and percentage PO display field 352 displays the total amount of fluid taken by mouth and determines what percentage of enteral nutrition of the total volume was taken in by mouth. The total enteral nutrition module 350 may generate a total enteral nutrition volume display 354 that displays the total amount or volume of enteral nutrition received by the infant for a given time period. A total enteral nutrition by weight display field 356 may be included that displays the total amount of fluid received by the infant in relation to the infants actual body weight (i.e.—Total enteral nutrition volume/actual body weight). A total enteral nutrition by dosing weight display field 358 may be included that displays the total amount of fluid received by the infant in relation to the dosing weight (i.e.—Total enteral nutrition volume/dosing weight).

The total enteral nutrition module 350 may also automatically display a total enteral nutrition calorie display 360. The total enteral nutrition calorie display 360 displays a data value associated with the sum of all of the calories the infant received over a predetermined time period from enteral nutrition intake. A total enteral nutrition calorie by weight display field 362 may be included that displays the amount of calories taken in by the infant in relation to the infant's actual body weight for a respective time period. A total enteral nutrition calorie by dosing weight display 364 may also be included that automatically displays the amount of calories taken in by the infant in relation to the dosing weight prescribed for that time period. A total projected enteral nutrition volume display field 366 may also be included that uses a total projected calorie figure to automatically display the total projected enteral volume associated with obtaining that calorie figure. The total projected enteral calorie figure is manually entered in a total projected enteral calorie field 368.

The total enteral nutrition module 350 may also include a total enteral nutrition protein by body weight display field 370. The value of this field is automatically calculated by the NNA software application 14 based on the sum of all of the protein received by the infant divided by the infant's body weight. As with other embodiments, the columns in the enteral nutrition GUI 300 represent days, but may represent other periods of time. The total enteral nutrition module 350 may also be capable of calculating the average enteral nutrition protein received by the infant over a predetermined time period or date range. A time period data entry field 372 and a start date data entry field 374 may be included so that the user can designate the time period for which to determine the average protein received through enteral nutrition. An average enteral nutrition protein display field 376 may be included that automatically displays the average protein received by the infant through enteral nutrition over the chosen time period.

The total enteral nutrition module 350 may also be capable of automatically calculating the total protein received by enteral nutrition based on dosing weight and/or actual weight. This is equal to the sum of all protein received divided by the dosing weight. A total enteral nutrition protein display field 378 may be included to display the results. The total enteral nutrition module 350 may also be capable of calculating the average protein received by enteral nutrition based on dosing weight and/or actual weight over a predetermined time period or date range. A time period data entry field 380 and a start date data entry field 382 may be included so that the user can designate the time period for which to determine average enteral nutrition protein. An average enteral nutrition protein intake by dosing weight display field 384 may be included to display the average protein received by the infant based on dosing weight and/or actual weight through enteral nutrition over the chosen time period.

Figure 14:
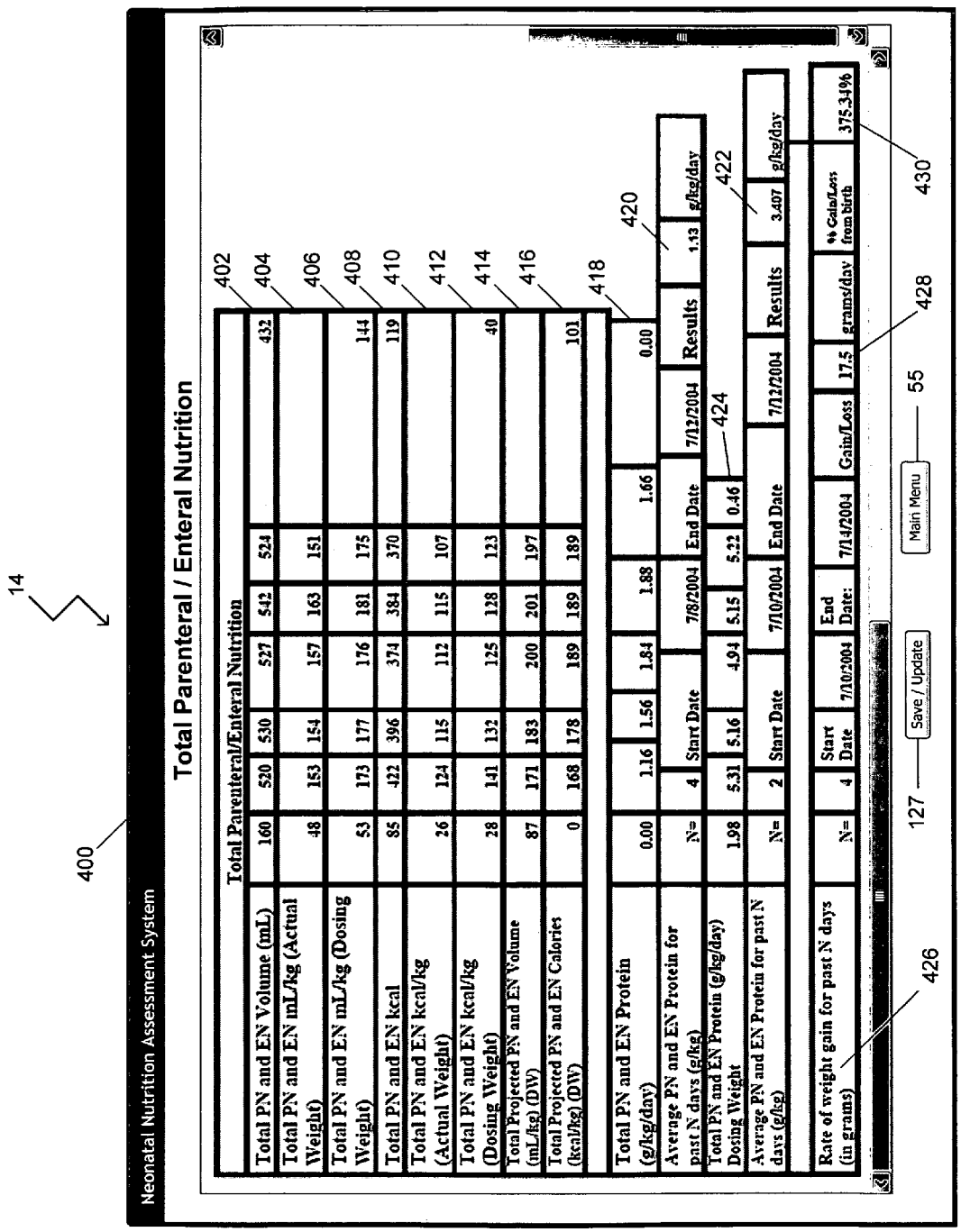
FIG. 14 represents an illustrative total parenteral and enteral nutrition graphical user interface of the NNA software application.

Referring to FIG. 4 and 14, the main menu GUI 60 may also include the total parenteral and enteral nutrition ("PEN") module 70. The total PEN module 70 may be operable to automatically generate a total PEN GUI 400. The total PEN GUI 400 may include a total PEN volume display field 402, a total PEN volume by weight display field 404, a total PEN volume by dosing weight display field 406, a total PEN calorie display field 408, a total PEN calorie by weight display field 410, a total PEN calorie by dosing weight display field 412, a total projected PEN volume display field 414, and a total projected PEN calorie display field 416. As in the previous examples, the data in the total PEN GUI 400 may be illustrated in a column format wherein each individual column represents a given time period or day.

The total PEN module 70 may display the total volume of fluid received by the infant over the time period through PEN feedings in the total PEN volume display field 402. The total PEN volume by weight display field 404 may provide a data value associated with the amount of fluid received by the infant in relation to the infant's actual body weight (e.g.— Total parenteral and enteral volume/Infants actual body weight). The total PEN volume by dosing weight display field 406 may provide a data value associated with the amount of fluid received by the infant as a function of the dosing weight (e.g.—Total parenteral and enteral volume/dosing weight).

The total PEN calorie display field 408 automatically displays the total amount of calories the infant received over a given time period from parenteral and enteral nutrition sources. The total PEN calorie by weight display field 410 may provide a data value associated with the amount of calories received by the infant in relation to the infant's actual body weight (e.g.—Total parenteral and enteral calories/Infants actual body weight). The total PEN calorie by dosing weight display field 412 may provide a data value associated with the amount of calories received by the infant as a function of the dosing weight (e.g.—Total parenteral and enteral calories/Dosing weight). The total projected PEN volume display field 414 and the total projected PEN calorie display field 416 represent the sums of the total projected parenteral volumes or calories plus the total projected enteral volumes or calories previously discussed in relation to parenteral and enteral nutrition.

The total PEN module 70 may also be operable to calculate the total enteral and parenteral protein received by the infant over a given time period (e.g.—every day). A total PEN protein display field 418 may be included that provides the amount of protein provided to the infant in relation to its actual body weight for a given day. An average PEN protein by weight display field 420 and an average PEN protein by dosing weight display field 422 may be included that are calculated similarly to other fields relating to just parenteral or enteral nutrition except that the values used consist of the sums of the previously computed data values. A total PEN protein dosing weight display field 424 may also be included for computing the total PEN protein dosing weight for a respective time period. A rate of weight gain display field 426 may be included that includes a weight gain/loss per day display field 428 and a percentage gain/loss display field 430.

Referring to FIGS. 4 and 15, as previously set forth the main menu GUI 60 may also include a medications module 72. Selection of the medications module 72 may cause the NNA software application 14 to generate a medications GUI 500. The medications GUI 500 may include a nutritional medications data input display 502 and a non-nutritional medications data input display 504. The nutritional medications data input display 502 may include a nutritional medication list 506, a dosage input field 508 and a date input field 510. As illustrated, the nutritional medication list 506 may contain various nutritional medications that may be prescribed to the infant. Associated with each medication in the nutritional medication list 506 is a respective dosage input field and a date input field 510. This allows the physician or caretaker to record and keep track of medications that are given to the infant, the associated dosage amounts, and the dates given. As further illustrated, the non-nutritional medication data input display 504 may be setup in the same manner.

Figure 16:
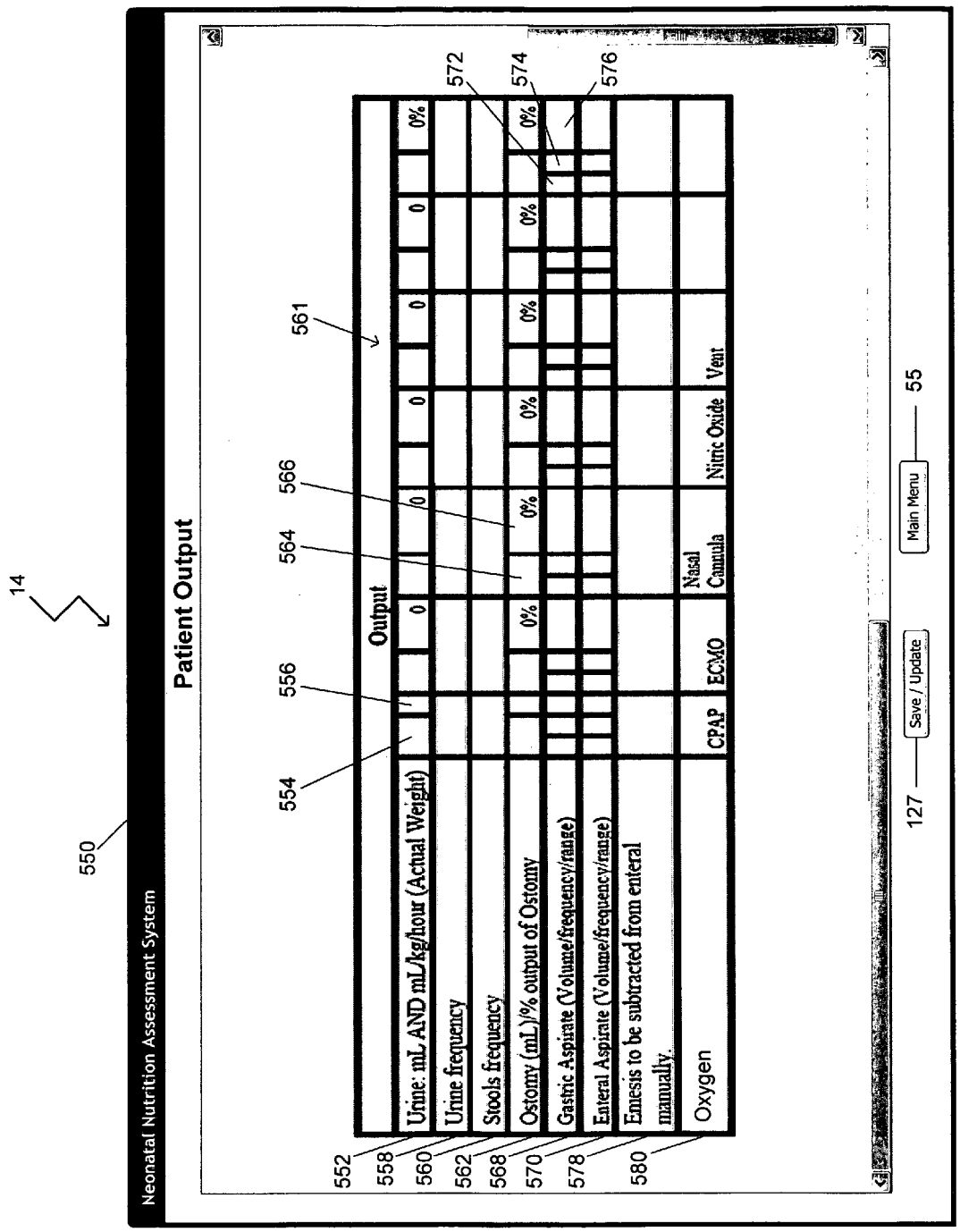
FIG. 16 represents an illustrative outputs graphical user interface of the NNA software application.

Referring to FIGS. 4 and 16, the main menu GUI 60 may also include the outputs module 74. Selection of the outputs module 74 may generate an outputs GUI 550 on the tablet PC 14. The outputs GUI 550 may include a urine output display field 552. The urine output display field 552 may include a volume input field 554 and an output field 556. The volume input field 554 is a manually entered field that allows the user to enter the volume of urine output of the infant. The volume input field 554 may be entered over a predetermined time period such as, for example, twice a day. The output field 556 may display the urine output of the infant as a function of the weight of the infant over the predetermined time period (e.g.—mL/kg/hour (actual weight and/or dosing weight)).

The outputs GUI 550 may also include a urine frequency input field 558 and a stools frequency input field 560. The urine frequency input field 558 and the stools frequency input field 560 allow the user to enter the number of times an event (i.e.—urination or stool) occurs over the predetermined time period, which as in previous embodiments, may be represented by columns 561 in the outputs GUI 550. The outputs GUI 550 may also include an ostomy display field 562, which may allow the user to record the volume of fluid removed from the infant through an artificial passageway created on the infant. The ostomy display field 562 may include a ostomy volume input field 564 and an ostomy percentage output field 566. The ostomy volume input field 564 may allow the user to enter the amount or volume of fluid that was removed from the infant. The ostomy percentage output field 566 may automatically display the percentage output of ostomy as a function of the total volume of enteral nutrition that entered the infant's body and the amount entered in the ostomy volume input field 564.

The outputs GUI 550 may also include a gastric aspirate display field 568 and an enteral aspirate display field 570. The gastric aspirate display field 568 and the enteral aspirate display field 570 may include a volume input field 572, a frequency input field 574 and a range input field 576. These data values are manually entered by the user of the NNA software application 14 and as with all other data associated with the infant, may be stored in the database 53. The outputs GUI 550 may also include a emesis to be subtracted data input field 578. The emesis to be subtracted data input field 578 allows the nutritional intake calculations to be more accurate and is subtracted from the total enteral nutritional intake. The outputs GUI 550 may also include an oxygen data input field 580 that relates to the medical well being of the patient.

Figure 17:
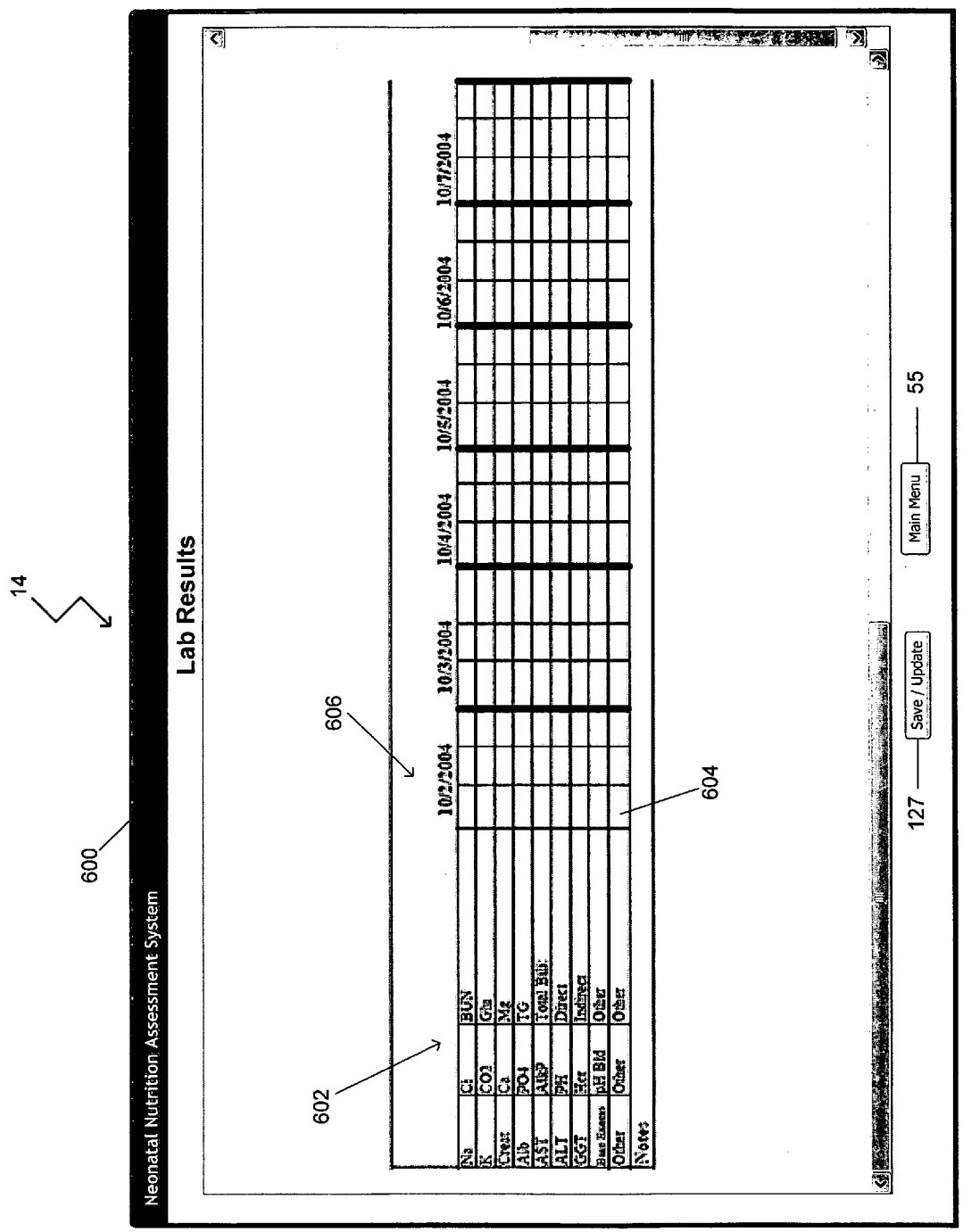
FIG. 17 represents an illustrative lab value graphical user interface of the NNA software application.

Referring to FIGS. 1, 4 and 17, the main menu GUI 60 may also include a lab value module 76. The NNA software application 14 may be connected with a lab server 27. As set forth above, most modern hospitals utilize laboratory software applications that automatically record test results in a predetermined format and store them in a database. The NNA software application 14 may pull this data from these software applications and generate a lab value GUI 600. The lab value module 76 may interface with the laboratory software application and automatically populate the lab value GUI 600 based on recent lab results.

In alternative embodiments of the present invention, the lab value GUI 600 may be used to manually enter lab values associated with the patient. The lab value GUI 600 may include a test result list 602 that may include a plurality of different types of tests. The lab value GUI 600 may also include a plurality of lab value input fields 604 that allow the user to manually enter lab result values in each respective lab value input field 604. As with previous embodiments, the lab value input fields 604 may be presented in columns 606 that are associated with different days or time periods.

Figure 18:
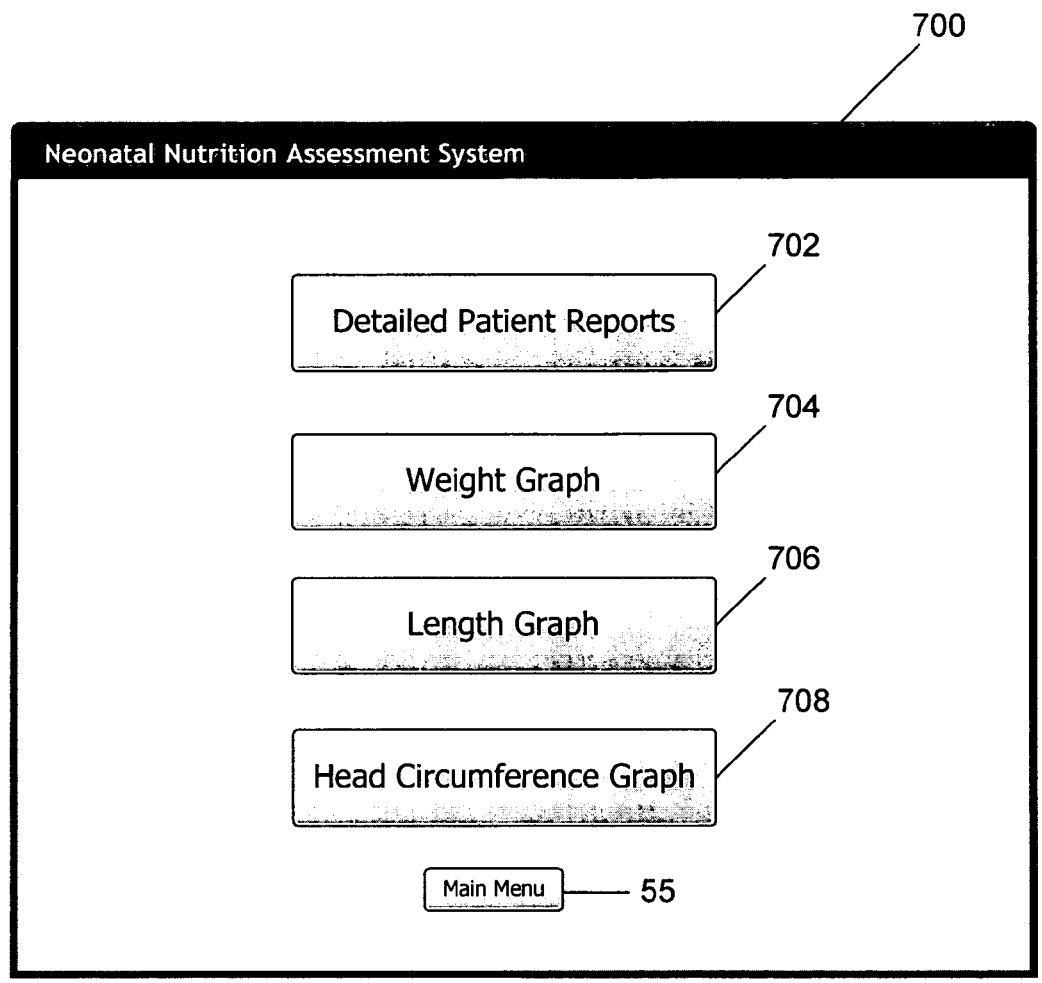
FIG. 18 represents an illustrative reports and graphs graphical user interface of the NNA software application.

Referring to FIGS. 4 and 18, selection of the reports and graphs module 78 in the Main Menu GUI 60 may generate a reports and graphs GUI 700. The reports and graphs GUI 700 may include a detailed report module 702, a weight graph module 704, a length graph module 706, and a head circumference graph module 708. Although not specifically illustrated, the print detailed report module 702 may allow a user of the NNA software application 14 to print out detailed patient reports. The patient reports may be selected and generated for any given patient using data from or relating to patient demographic reports, rate of weight gain reports, physician diagnosis reports, patient age and growth reports, parenteral nutrition reports, enteral nutrition reports, total parenteral and enteral nutrition reports, medication reports, output reports, and lab value reports. The format of the reports may vary and data contained in the reports may be retrieved by the detailed report module 702 from the patient database 53 for each given patient. The reports may be viewed in a GUI generated by the detailed reports module 702 and may also be printed by a user selected printer.

Figure 19:
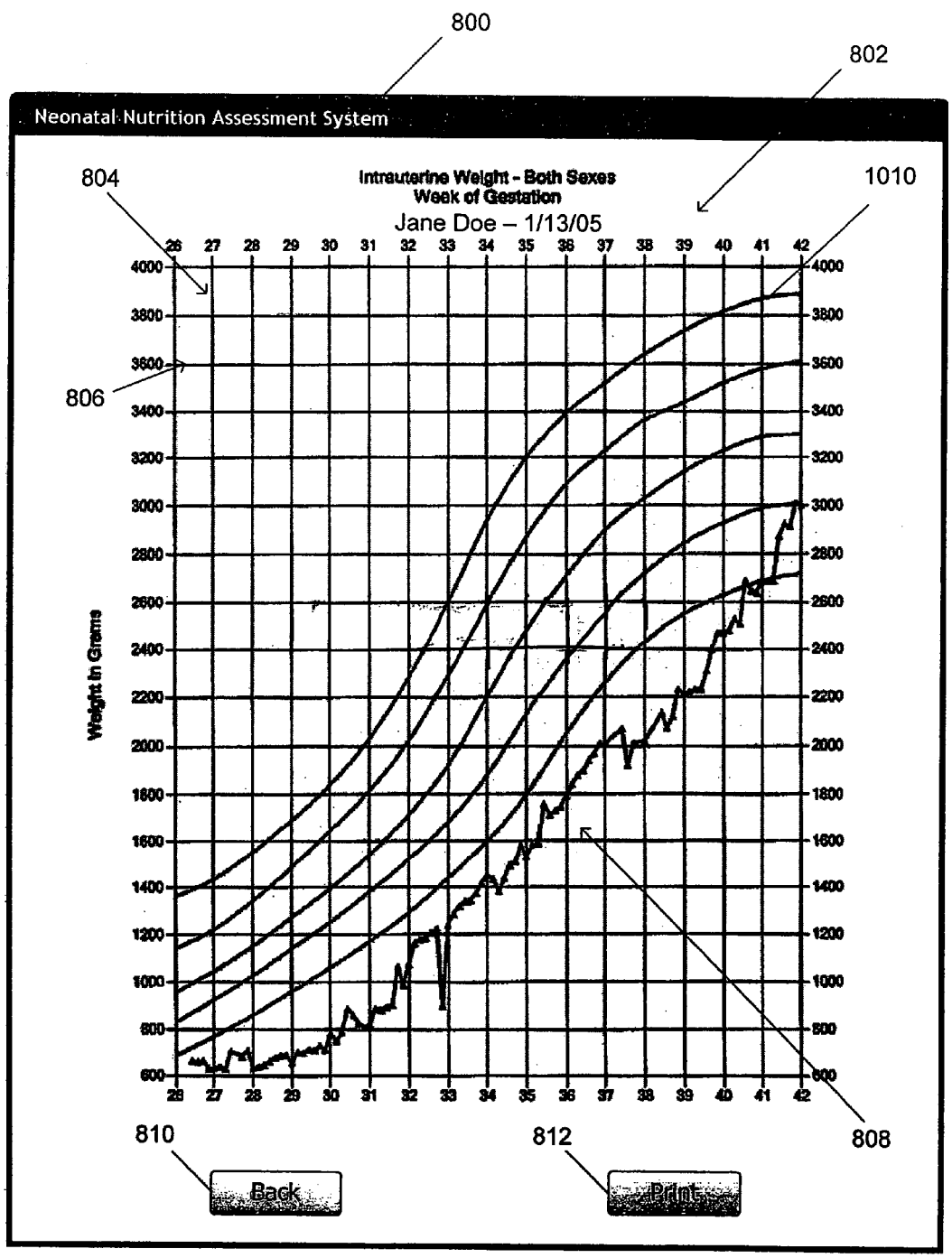
FIG. 19 represents an illustrative weight graph graphical user interface of the NNA software application.

As illustrated in FIGS. 18 and 19, selection of the weight graph module 704 in the reports and graphs GUI 700 may cause the NNA software application 14 to generate a weight graph GUI 800. As illustrated, the weight graph GUI 800 may contain a weight graph 802 that may automatically be generated by the weight graph module 704. To generate the weight graph 802, the weight graph module 704 may retrieve weight data (see FIG. 7 element 140) from the patient database 53. The vertical columns 804 may represent a week of gestation and the horizontal columns 806 may represent the patient's weight (preferentially grams). As such, a patient weight plot 808 may be generated on the weight graph 802 as a function of the patient's weight over time (i.e.—weight at each gestational week). A back button 810 may be included for taking the user back to the reports and graphs GUI 700 and a print button 812 may be included for printing out the weight graph 802 on a printer.

Figure 20:
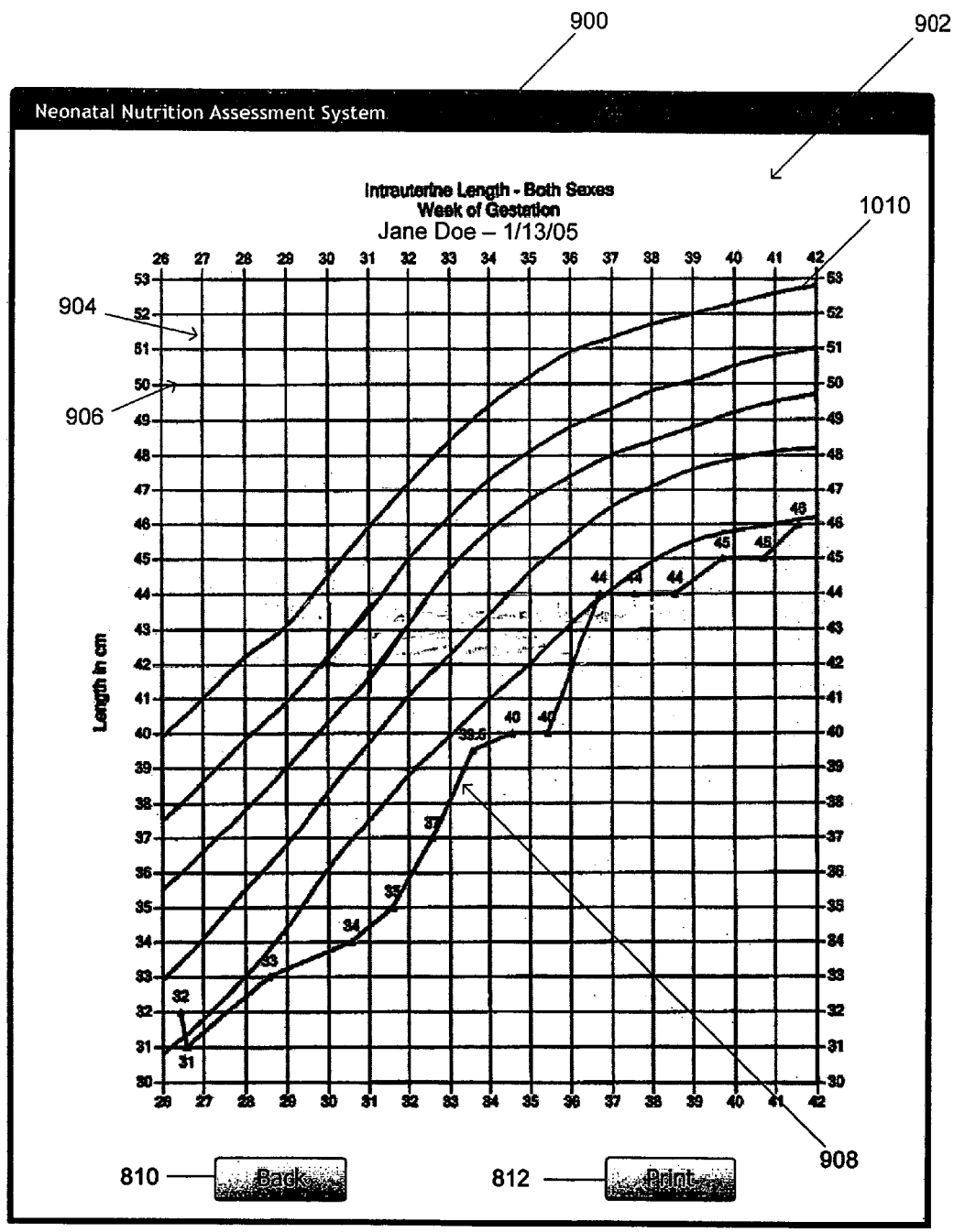
FIG. 20 represents an illustrative length graph graphical user interface of the NNA software application.

As illustrated in FIGS. 18 and 20, selection of the length graph module 706 in the reports and graphs GUI 700 may cause the NNA software application 14 to generate a length graph GUI 900. As illustrated, the length graph GUI 900 may contain a length graph 902 that may automatically be generated by the length graph module 706. To generate the length graph 902, the length graph module 706 may retrieve length data (see FIG. 7 element 144) from the patient database 53. The vertical columns 904 may represent a week of gestation and the horizontal columns 906 may represent the patient's weight (preferentially centimeters). As such, a patient length plot 908 may be generated on the length graph 902 as a function of the patient's length over time (i.e.—length at each gestational week). A back button 810 may be included for taking the user back to the reports and graphs GUI 700 and a print button 812 may be included for printing out the length graph 902 on a printer.

Figure 21:
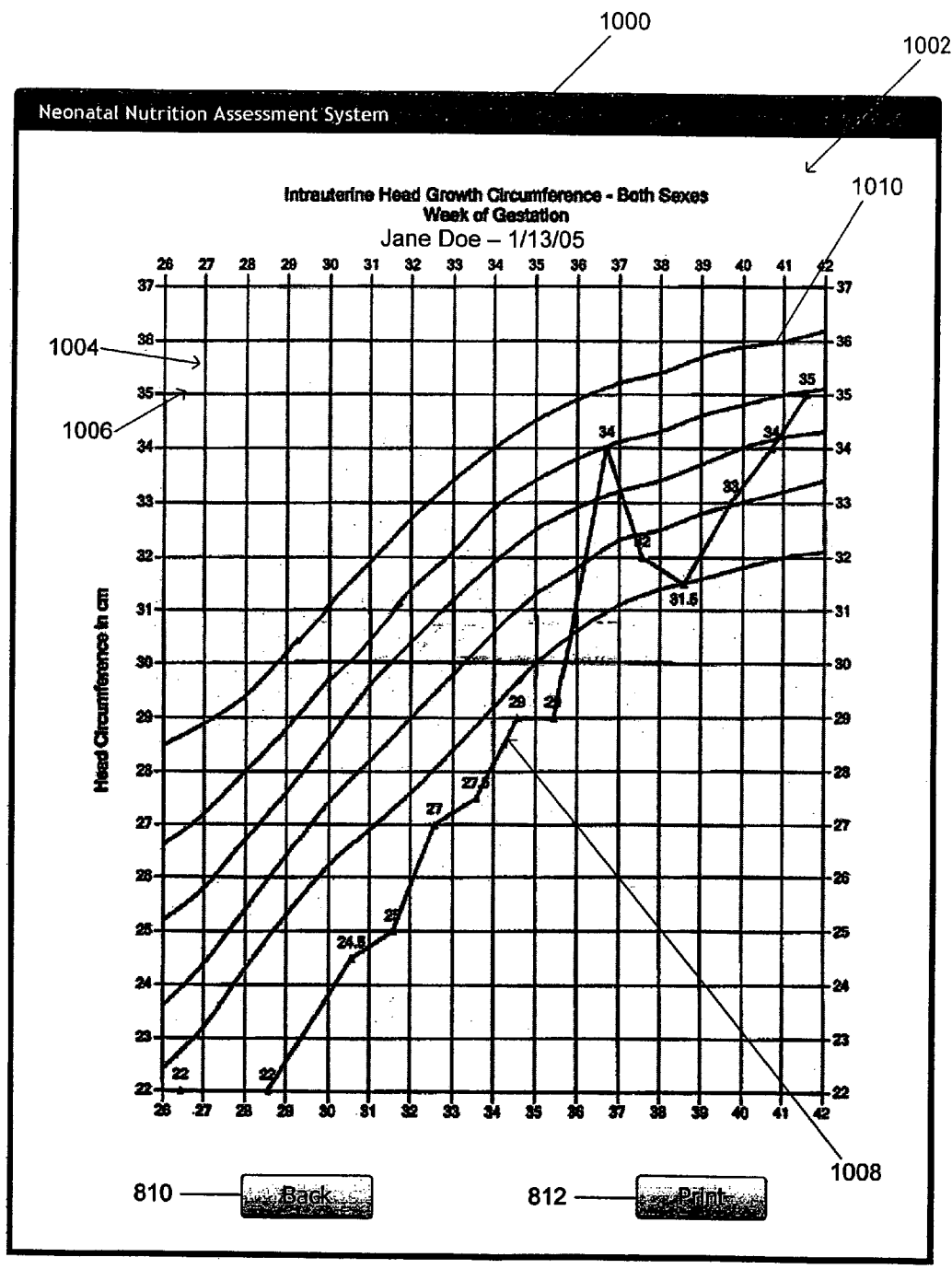
FIG. 21 represents an illustrative head circumference graph graphical user interface of the NNA software application.

As illustrated in FIGS. 18 and 21, selection of the head circumference graph module 708 in the reports and graphs GUI 700 may cause the NNA software application 14 to generate a head circumference graph GUI 1000. As illustrated, the head circumference graph GUI 1000 may contain a head circumference graph 1002 that may automatically be generated by the head circumference graph module 708. To generate the head circumference graph 1002, the head circumference module 708 may retrieve head circumference data (see FIG. 7 element 142) from the patient database 53. The vertical columns 1004 may represent a week of gestation and the horizontal columns 1006 may represent the patient's weight (preferentially centimeters). As such, a head circumference plot 1008 may be generated on the head circumference graph 1002 as a function of the patient's head circumference over time (i.e.—head circumference at each gestational week). A back button 810 may be included for taking the user back to the reports and graphs GUI 700 and a print button 812 may be included for printing out the head circumference graph 1002 on a printer. Those skilled in the art would recognize that various other types of graphs and reports may be generated by the present invention. To that end, the graphs and charts illustrated herein should be viewed in an illustrative and not restrictive sense.

Referring to FIGS. 19-21, a plurality of normative data values 1010 are given on each respective graph that allows a caretaker to view the progress of the patient in relation to other normal infants. The caretaker can use this data in providing treatment to the respective infant and to track the progress of the infant. The National Academy of Sciences comes out with nutrient recommendations for different types of populations about every five years. The present invention allows a caretaker to come prescribe enteral and parenteral nutrition orders that provide patients with enough nutrients.

While the present invention has been described with reference to specific exemplary embodiments, it will be evident that various modifications and changes may be made to these embodiments without departing from the broader spirit and scope of the invention as set forth in the claims. Accordingly, the specification and drawings are to be regarded in an illustrative rather than a restrictive sense.

What is claimed is:

1. A method of providing nutritional assessment for patients in an intensive care unit, comprising the steps of:
   recording a parenteral nutrition prescription prescribed to said patient in said patient database server;
   recording an enteral nutrition prescription prescribed to said patient in said patient database server;
   calculating a plurality of nutritional data values associated with said parenteral nutrition prescription and said enteral nutrition prescription as a function of an actual amount of parenteral and enteral nutrition delivered and an actual amount of nutrition removed or otherwise not retained by said patient; and
   presenting said nutritional data values to a caretaker through a graphical user interface generated on a remote terminal connected with said patient database server.

2. The method of claim 1, comprising the further step of calculating an amount of calories associated with the nutrition, the actual amount of parenteral and enteral nutrition delivered being in the form of the calculated calories.

3. The method of claim 2, comprising the further step of calculating and displaying a total number of parenteral calories per dosing weight.

4. A method of providing nutritional assessment for patients in an intensive care unit, comprising the steps of:
- recording a parenteral nutrition prescription prescribed to a patient in a patient database server;
- recording an enteral nutrition prescription prescribed to said patient in said patient database server;
- determining an actual amount of parenteral and enteral nutrition delivered and an actual amount of nutrition removed or otherwise not retained by said patient;
- calculating a plurality of nutritional data values associated with said parenteral nutrition prescription and said enteral nutrition prescription as a function of the actual amount of parenteral and enteral nutrition delivered and an actual amount of nutrition removed or otherwise not retained by said patient; and
- presenting said nutritional data values to a caretaker through a graphical user interface generated on a remote terminal connected with said patient database server.

5. The method of claim 4, comprising the further step of recording a diagnosis of said patient in the patient database server, the prescriptions being dependent upon the recorded diagnosis.

6. The method of claim 4, comprising the further steps of:
- recording an infusion rate associated with at least one of the parenteral nutrition prescription and the enteral nutrition prescription; and
- automatically calculating and displaying a percentage of the prescription relative to the infusion rate.

7. The method of claim 1, wherein the nutritional data values are calculated as a function of a weight of said patient after the actual amount of parenteral and enteral nutrition is delivered and retained by said patient.

8. The method of claim 7, wherein the nutritional data values are employed to benefit said same patient whose weight that the calculation of the nutritional data values is based on.

9. The method of claim 1, wherein the nutritional data values are calculated as a function of a rate of weight gain of said patient after the actual amount of parenteral and enteral nutrition is delivered and retained by said patient.

10. The method of claim 9, comprising the further steps of:
- a user entering a start date and an end date of the weight gain; and
- automatically calculating an average weight gain per day between the start date and the end date, wherein the nutritional data values are calculated as a function of the calculated average weight gain per day of said patient after the actual amount of parenteral and enteral nutrition is delivered and retained by said patient.

11. The method of claim 1, wherein the nutritional data values are calculated as a function of a bodily function of said patient.

12. The method of claim 11, wherein the bodily function comprises a renal function of said patient.

* * * * *